United States Patent
Bitar et al.

(10) Patent No.: US 10,799,646 B2
(45) Date of Patent: Oct. 13, 2020

(54) INJECTION DEVICE

(71) Applicant: Cilag GmbH International, Zug (CH)

(72) Inventors: Ahmad Bitar, Cambridgeshire (GB); Douglas Ivan Jennings, Hertfordshire (GB)

(73) Assignee: Cilag GmbH International, Zug (CH)

( * ) Notice: Subject to any disclaimer, the term of this patent is extended or adjusted under 35 U.S.C. 154(b) by 672 days.

(21) Appl. No.: 14/897,360

(22) PCT Filed: Jun. 11, 2014

(86) PCT No.: PCT/EP2014/062166
§ 371 (c)(1),
(2) Date: Dec. 10, 2015

(87) PCT Pub. No.: WO2014/198797
PCT Pub. Date: Dec. 18, 2014

(65) Prior Publication Data
US 2016/0106924 A1    Apr. 21, 2016

(30) Foreign Application Priority Data

Jun. 11, 2013 (GB) .................................. 1310389.0

(51) Int. Cl.
*A61M 5/315* (2006.01)
*A61M 5/20* (2006.01)
*A61M 5/32* (2006.01)

(52) U.S. Cl.
CPC ........ *A61M 5/3157* (2013.01); *A61M 5/2033* (2013.01); *A61M 5/3202* (2013.01);
(Continued)

(58) Field of Classification Search
CPC .............. A61M 5/3157; A61M 5/2033; A61M 5/3202; A61M 5/31535;
(Continued)

(56) References Cited

U.S. PATENT DOCUMENTS 1,845,036 A    2/1932 Busher
2,019,382 A    10/1935 Aronson
(Continued)

FOREIGN PATENT DOCUMENTS

CA    2445511 A1    11/2002
CH    518102 A    1/1972
(Continued)

OTHER PUBLICATIONS

Page entitled 'Unusual cams' V. Ryan, 2002-2009; from www.technologystudent.com.
(Continued)

*Primary Examiner* — Nathan R Price
*Assistant Examiner* — John A Doubrava
(74) *Attorney, Agent, or Firm* — Steven J. Schwarz

(57) ABSTRACT

An injection device for delivering an injection comprises a housing having a longitudinal axis, a proximal end and a distal end, the housing being arranged such that the injection is delivered from its distal end; and a release mechanism comprising an impediment, the release mechanism being moveable between a first position, in which the impediment is in an impeding position so as to impede the delivery of the injection, and a second position, in which the impediment is in a non-impeding position so as to not impede the delivery of the injection, wherein the force required to move the release mechanism from the first position to the second position varies with the distance moved by the release mechanism, the variation in the force required with distance being represented by a force profile, which is non-linear.

17 Claims, 11 Drawing Sheets

(52) U.S. Cl.
CPC ............... *A61M 2005/2006* (2013.01); *A61M 2005/206* (2013.01); *A61M 2005/208* (2013.01); *A61M 2205/581* (2013.01)

(58) Field of Classification Search
CPC .... A61M 2005/2006; A61M 2005/206; A61M 2005/208; A61M 2205/581
See application file for complete search history.

(56) References Cited

U.S. PATENT DOCUMENTS

| | | |
|---|---|---|
| 2,147,616 A | 2/1939 | Chaput |
| 2,295,849 A | 9/1942 | Kayden |
| 2,531,267 A | 11/1950 | Harisch |
| 2,752,918 A | 7/1956 | Rooseboom |
| 2,764,977 A | 10/1956 | Ferguson |
| 2,828,742 A | 4/1958 | Ashkenaz |
| 2,845,065 A | 7/1958 | Gabriel |
| 2,854,975 A | 10/1958 | Cohen |
| 3,076,455 A | 2/1963 | McConnaughey et al. |
| 3,131,692 A | 5/1964 | Love |
| 3,320,955 A | 5/1967 | Sarnoff |
| 3,329,146 A | 7/1967 | Waldman |
| 3,543,603 A | 12/1970 | Gley |
| 3,656,472 A | 4/1972 | Ben Moura |
| 3,674,033 A | 7/1972 | Powers |
| 3,702,608 A | 11/1972 | Tibbs |
| 3,742,948 A | 7/1973 | Post et al. |
| 3,797,488 A | 3/1974 | Hurschman et al. |
| 3,797,489 A | 3/1974 | Sarnoff |
| 3,880,163 A | 4/1975 | Ritterskamp |
| 3,976,069 A | 8/1976 | Ong |
| 4,165,739 A | 8/1979 | Doherty et al. |
| 4,180,070 A | 12/1979 | Genese |
| 4,185,628 A | 1/1980 | Kopfer |
| 4,194,505 A | 3/1980 | Schmitz |
| 4,222,380 A | 9/1980 | Terayama |
| 4,231,368 A | 11/1980 | Becker |
| 4,236,516 A | 12/1980 | Nilson |
| 4,237,882 A | 12/1980 | Wickham |
| 4,299,238 A | 11/1981 | Baidwan et al. |
| 4,333,459 A | 6/1982 | Becker |
| 4,373,526 A | 2/1983 | Kling |
| 4,378,015 A | 3/1983 | Wardlaw |
| 4,394,863 A | 7/1983 | Bartner |
| 4,403,989 A | 9/1983 | Christensen et al. |
| 4,407,283 A | 10/1983 | Reynolds |
| 4,425,120 A | 1/1984 | Sampson et al. |
| 4,430,082 A | 2/1984 | Schwabacher |
| 4,500,310 A | 2/1985 | Christinger |
| 4,507,118 A | 3/1985 | Dent |
| 4,521,237 A | 6/1985 | Logothetis |
| 4,561,856 A | 12/1985 | Cochran et al. |
| 4,627,835 A | 12/1986 | Fenton, Jr. |
| 4,636,201 A | 1/1987 | Ambrose et al. |
| 4,639,250 A | 1/1987 | Rycroft |
| 4,642,099 A | 2/1987 | Phillips et al. |
| 4,676,530 A | 6/1987 | Nordgren et al. |
| 4,695,274 A | 9/1987 | Fox |
| 4,717,383 A | 1/1988 | Phillips et al. |
| 4,744,786 A | 5/1988 | Hooven et al. |
| 4,787,891 A | 11/1988 | Levin et al. |
| 4,874,383 A | 10/1989 | McNaughton |
| 4,874,384 A | 10/1989 | Nunez |
| 4,929,232 A | 5/1990 | Sweeney et al. |
| 4,969,870 A | 11/1990 | Kramer et al. |
| 4,988,339 A | 1/1991 | Vadher |
| 4,994,034 A | 2/1991 | Botich et al. |
| 5,009,646 A | 4/1991 | Sudo et al. |
| 5,026,349 A | 6/1991 | Schmitz et al. |
| 5,057,079 A | 10/1991 | Tiemann et al. |
| 5,073,170 A | 12/1991 | Schneider |
| 5,092,842 A | 3/1992 | Bechtold et al. |
| 5,098,400 A | 3/1992 | Crouse et al. |
| 5,112,119 A | 5/1992 | Cooke et al. |
| 5,114,406 A | 5/1992 | Gabriel et al. |
| 5,122,119 A | 6/1992 | Lucas |
| 5,137,516 A | 8/1992 | Rand et al. |
| 5,141,496 A | 8/1992 | Dalto et al. |
| 5,147,325 A | 9/1992 | Mitchell et al. |
| 5,156,599 A | 10/1992 | Ranford et al. |
| 5,176,643 A | 1/1993 | Kramer et al. |
| 5,188,613 A | 2/1993 | Shaw |
| 5,190,526 A | 3/1993 | Murray et al. |
| 5,242,400 A | 9/1993 | Blake et al. |
| 5,242,416 A | 9/1993 | Hutson |
| 5,250,026 A | 10/1993 | Ehrlich et al. |
| 5,250,037 A | 10/1993 | Bitdinger |
| 5,263,933 A | 11/1993 | Novacek et al. |
| 5,267,963 A | 12/1993 | Bachynsky |
| 5,271,744 A | 12/1993 | Kramer et al. |
| 5,295,965 A | 3/1994 | Wilmot |
| 5,300,030 A | 4/1994 | Crossman et al. |
| 5,312,364 A | 5/1994 | Jacobs |
| 5,330,081 A | 7/1994 | Davenport |
| 5,330,430 A | 7/1994 | Sullivan |
| 5,356,395 A | 10/1994 | Chen |
| 5,358,489 A | 10/1994 | Wyrick |
| 5,364,369 A | 11/1994 | Reynolds |
| 5,368,577 A | 11/1994 | Teoh et al. |
| 5,372,586 A | 12/1994 | Haber et al. |
| 5,385,551 A | 1/1995 | Shaw |
| 5,391,151 A | 2/1995 | Wilmot |
| 5,405,362 A | 4/1995 | Kramer et al. |
| 5,411,488 A | 5/1995 | Pagay et al. |
| 5,425,715 A | 6/1995 | Dalling et al. |
| 5,451,210 A | 9/1995 | Kramer et al. |
| 5,478,316 A | 12/1995 | Bitdinger et al. |
| 5,480,387 A | 1/1996 | Gabriel et al. |
| 5,487,732 A | 1/1996 | Jeffrey |
| 5,489,256 A | 2/1996 | Adair |
| 5,503,627 A | 4/1996 | McKinnon et al. |
| 5,514,097 A | 5/1996 | Knauer |
| 5,520,653 A | 5/1996 | Reilly et al. |
| 5,540,660 A | 7/1996 | Jenson et al. |
| 5,540,666 A | 7/1996 | Barta et al. |
| 5,540,709 A | 7/1996 | Ramel et al. |
| 5,567,160 A | 10/1996 | Massino |
| 5,569,191 A | 10/1996 | Meyer |
| 5,569,192 A | 10/1996 | van der Wal |
| 5,575,777 A | 11/1996 | Cover et al. |
| 5,599,302 A | 2/1997 | Lilley et al. |
| 5,599,309 A | 2/1997 | Marshall et al. |
| 5,607,395 A | 3/1997 | Ragsdale et al. |
| 5,609,577 A | 3/1997 | Haber et al. |
| 5,609,584 A | 3/1997 | Gettig et al. |
| 5,611,785 A | 3/1997 | Mito et al. |
| 5,634,906 A | 6/1997 | Foster et al. |
| 5,637,094 A | 6/1997 | Stewart, Jr. et al. |
| 5,645,536 A | 7/1997 | Whisson |
| 5,647,845 A | 7/1997 | Haber et al. |
| 5,649,912 A | 7/1997 | Peterson |
| 5,658,259 A | 8/1997 | Pearson et al. |
| 5,665,071 A | 9/1997 | Wyrick |
| 5,681,291 A | 10/1997 | Galli |
| 5,697,908 A | 12/1997 | Imbert |
| 5,702,367 A | 12/1997 | Cover et al. |
| 5,704,911 A | 1/1998 | Parsons et al. |
| 5,709,662 A | 1/1998 | Olive et al. |
| 5,713,866 A | 2/1998 | Wilmot |
| 5,748,316 A | 5/1998 | Wakabayashi et al. |
| 5,779,668 A | 7/1998 | Grabenkort |
| 5,779,677 A | 7/1998 | Frezza |
| 5,807,334 A | 9/1998 | Hodosh et al. |
| 5,817,058 A | 10/1998 | Shaw |
| 5,827,262 A | 10/1998 | Neftel et al. |
| 5,843,036 A | 12/1998 | Olive et al. |
| 5,855,839 A | 1/1999 | Brunel |
| 5,865,795 A | 2/1999 | Schiff et al. |
| 5,865,804 A | 2/1999 | Bachynsky |
| 5,868,711 A | 2/1999 | Kramer et al. |
| 5,879,327 A | 3/1999 | Moreau DeFarges et al. |
| 5,891,086 A | 4/1999 | Terrence et al. |
| 5,913,843 A | 6/1999 | Jentzen |

(56) References Cited

U.S. PATENT DOCUMENTS

| | | | |
|---|---|---|---|
| 5,928,205 A | 7/1999 | Marshall | |
| 5,954,738 A | 9/1999 | LeVaughn et al. | |
| 5,957,897 A | 9/1999 | Jeffrey | |
| 5,960,797 A | 10/1999 | Kramer et al. | |
| 5,989,229 A | 11/1999 | Chiappetta | |
| 5,997,513 A | 12/1999 | Smith et al. | |
| 6,007,515 A | 12/1999 | Epstein et al. | |
| 6,015,438 A | 1/2000 | Shaw | |
| 6,017,330 A | 1/2000 | Hitchins et al. | |
| 6,036,675 A | 3/2000 | Thorne et al. | |
| 6,045,534 A | 4/2000 | Jacobsen et al. | |
| 6,068,614 A | 5/2000 | Kimber et al. | |
| 6,077,247 A | 6/2000 | Marshall et al. | |
| 6,083,197 A | 7/2000 | Umbaugh | |
| 6,086,562 A | 7/2000 | Jacobsen et al. | |
| 6,090,070 A | 7/2000 | Hager et al. | |
| 6,090,078 A | 7/2000 | Erskine | |
| 6,090,897 A | 7/2000 | Akasaki et al. | |
| 6,099,503 A | 8/2000 | Stradella | |
| 6,099,504 A | 8/2000 | Gross | |
| 6,123,684 A | 9/2000 | Deboer et al. | |
| 6,139,534 A | 10/2000 | Niedospial, Jr. et al. | |
| 6,159,161 A | 12/2000 | Hodosh | |
| 6,159,181 A | 12/2000 | Crossman et al. | |
| 6,159,184 A | 12/2000 | Perez et al. | |
| 6,162,199 A | 12/2000 | Geringer | |
| 6,171,276 B1 | 1/2001 | Lippe et al. | |
| 6,179,812 B1 | 1/2001 | Botich et al. | |
| 6,186,980 B1 | 2/2001 | Brunel | |
| 6,190,363 B1 | 2/2001 | Gabbard et al. | |
| 6,193,696 B1 | 2/2001 | Jansen et al. | |
| 6,203,530 B1 | 3/2001 | Stewart | |
| 6,209,738 B1 | 4/2001 | Jansen et al. | |
| 6,221,044 B1 | 4/2001 | Grecco | |
| 6,228,055 B1 | 5/2001 | Foerster et al. | |
| 6,258,068 B1 | 7/2001 | Kirchhofer et al. | |
| 6,270,479 B1 | 8/2001 | Bergens et al. | |
| 6,280,421 B1 | 8/2001 | Kirchhofer et al. | |
| 6,290,683 B1 | 9/2001 | Erez et al. | |
| 6,293,925 B1 | 9/2001 | Safabash et al. | |
| RE37,439 E | 11/2001 | Firth et al. | |
| 6,317,939 B1 | 11/2001 | Malin | |
| 6,330,960 B1 | 12/2001 | Faughey et al. | |
| 6,332,875 B2 | 12/2001 | Inkpen et al. | |
| 6,371,939 B2 | 4/2002 | Bergens et al. | |
| 6,371,959 B1 | 4/2002 | Trice | |
| 6,387,078 B1 | 5/2002 | Gillespie | |
| 6,391,003 B1 | 5/2002 | Lesch | |
| 6,419,658 B1 | 7/2002 | Restelli et al. | |
| 6,428,528 B2 | 8/2002 | Sadowski et al. | |
| 6,447,480 B1 | 9/2002 | Brunel | |
| 6,454,743 B1 | 9/2002 | Weber | |
| 6,454,746 B1 | 9/2002 | Bydion et al. | |
| 6,461,333 B1 | 10/2002 | Frezza | |
| 6,491,667 B1 | 12/2002 | Keane et al. | |
| 6,517,517 B1 | 2/2003 | Farrugia et al. | |
| 6,536,723 B1 | 3/2003 | Nakatani | |
| 6,537,252 B1 | 3/2003 | Hansen | |
| 6,544,234 B1 | 4/2003 | Gabriel | |
| 6,565,540 B1 | 5/2003 | Perouse et al. | |
| 6,565,553 B2 | 5/2003 | Sadowski et al. | |
| 6,569,115 B1 | 5/2003 | Barker et al. | |
| 6,569,123 B2 | 5/2003 | Aichas et al. | |
| 6,569,124 B1 | 5/2003 | Perouse | |
| 6,572,581 B1 | 6/2003 | Landua | |
| 6,575,939 B1 | 6/2003 | Brunel | |
| 6,579,269 B1 * | 6/2003 | Kleyman | A61M 5/31555 604/207 |
| 6,585,702 B1 | 7/2003 | Brunel | |
| 6,589,210 B1 | 7/2003 | Rolfe | |
| 6,595,957 B1 | 7/2003 | Griffiths et al. | |
| 6,595,962 B1 | 7/2003 | Perthu | |
| 6,599,272 B1 | 7/2003 | Hjertman et al. | |
| 6,607,508 B2 | 8/2003 | Knauer | |
| 6,607,510 B2 | 8/2003 | Landau | |
| 6,613,022 B1 | 9/2003 | Doyle | |
| 6,620,137 B2 | 9/2003 | Kirchhofer et al. | |
| 6,638,256 B2 | 10/2003 | Jansen et al. | |
| 6,641,554 B2 | 11/2003 | Landau | |
| 6,641,560 B1 | 11/2003 | Bechtold et al. | |
| 6,641,565 B1 | 11/2003 | Lavi et al. | |
| 6,645,170 B2 | 11/2003 | Landua | |
| 6,645,181 B1 | 11/2003 | Lavi et al. | |
| 6,648,835 B1 | 11/2003 | Shemesh | |
| 6,648,850 B2 | 11/2003 | Landau | |
| 6,656,163 B1 | 12/2003 | Marshall et al. | |
| 6,673,049 B2 | 1/2004 | Hommann et al. | |
| 6,676,630 B2 | 1/2004 | Landau et al. | |
| 6,689,093 B2 | 2/2004 | Landau et al. | |
| 6,692,469 B1 | 2/2004 | Weekes et al. | |
| 6,699,220 B2 | 3/2004 | Rolfe | |
| 6,740,062 B2 | 5/2004 | Hjertman | |
| 6,743,199 B2 | 6/2004 | Shue et al. | |
| 6,743,203 B1 | 6/2004 | Pickhard et al. | |
| 6,746,429 B2 | 6/2004 | Sadowski et al. | |
| 6,746,438 B1 | 6/2004 | Arnissolle | |
| 6,767,336 B1 | 7/2004 | Kaplan | |
| 6,770,056 B2 | 8/2004 | Price et al. | |
| 6,776,777 B2 | 8/2004 | Barelle | |
| 6,783,509 B1 | 8/2004 | Landau et al. | |
| 6,793,161 B1 | 9/2004 | Fujia et al. | |
| 6,796,967 B2 | 9/2004 | Jensen | |
| 6,811,548 B2 | 11/2004 | Jeffrey | |
| 6,817,987 B2 | 11/2004 | Vetter et al. | |
| 6,846,303 B2 | 1/2005 | Eakins et al. | |
| 6,875,205 B2 | 4/2005 | Leinsing | |
| 6,890,319 B1 | 5/2005 | Crocker | |
| 6,899,698 B2 | 5/2005 | Sams | |
| 6,902,543 B1 | 6/2005 | Cherif-Cheikh et al. | |
| 6,932,793 B1 | 8/2005 | Marshall et al. | |
| 6,939,319 B1 | 9/2005 | Anstead et al. | |
| 6,939,330 B1 | 9/2005 | McConnell et al. | |
| 6,979,316 B1 | 12/2005 | Rubin et al. | |
| 7,066,907 B2 | 6/2006 | Crossman et al. | |
| 7,097,071 B2 | 8/2006 | Anderson et al. | |
| 7,097,634 B2 | 8/2006 | Gilbert | |
| 7,118,553 B2 | 10/2006 | Scherer | |
| 7,156,823 B2 | 1/2007 | Landau et al. | |
| 7,160,913 B2 | 1/2007 | Schneider | |
| 7,294,122 B2 | 11/2007 | Kubo et al. | |
| 7,354,427 B2 | 4/2008 | Fangrow | |
| RE40,428 E | 7/2008 | Keane et al. | |
| 7,442,185 B2 | 10/2008 | Amark et al. | |
| 7,470,258 B2 | 12/2008 | Barker et al. | |
| 7,507,227 B2 | 3/2009 | Fangrow | |
| 7,510,547 B2 | 3/2009 | Fangrow | |
| 7,510,548 B2 | 3/2009 | Fangrow | |
| 7,513,895 B2 | 4/2009 | Fangrow | |
| 7,534,238 B2 | 5/2009 | Fangrow | |
| 7,547,300 B2 | 6/2009 | Fangrow | |
| 7,569,043 B2 | 8/2009 | Fangrow | |
| 7,618,396 B2 | 11/2009 | Slate et al. | |
| 7,635,356 B2 | 12/2009 | Stamp | |
| 7,645,271 B2 | 1/2010 | Fangrow | |
| 7,654,995 B2 | 2/2010 | Warren et al. | |
| 7,658,733 B2 | 2/2010 | Fangrow | |
| 7,678,333 B2 | 3/2010 | Reynolds et al. | |
| 7,682,155 B2 | 3/2010 | Raven et al. | |
| 7,682,345 B2 | 3/2010 | Savage | |
| 7,717,879 B2 | 5/2010 | Mansouri | |
| 7,744,561 B2 | 6/2010 | Stamp | |
| 7,759,654 B2 | 7/2010 | Yan et al. | |
| 7,785,292 B2 | 8/2010 | Harrison | |
| 7,794,434 B2 | 9/2010 | Mounce et al. | |
| 7,799,009 B2 | 9/2010 | Niedospial, Jr. et al. | |
| 7,811,262 B2 | 10/2010 | Moberg et al. | |
| 7,828,764 B2 | 11/2010 | Moberg et al. | |
| 7,871,397 B2 | 1/2011 | Schraga | |
| 7,879,010 B2 | 2/2011 | Hunn et al. | |
| 7,883,499 B2 | 2/2011 | Fangrow | |
| 7,959,715 B2 | 6/2011 | Kavazov et al. | |
| 7,972,321 B2 | 7/2011 | Fangrow | |
| 7,976,499 B2 | 7/2011 | Grunhut et al. | |
| 8,100,154 B2 | 1/2012 | Reynolds et al. | |

(56) References Cited

U.S. PATENT DOCUMENTS

| | | |
|---|---|---|
| 8,177,768 B2 | 5/2012 | Leinsing |
| 8,277,414 B2 | 10/2012 | Barrow-Williams et al. |
| 8,313,463 B2 | 11/2012 | Barrow-Williams et al. |
| 8,317,751 B2 | 11/2012 | Alheidt |
| 8,343,110 B2 | 1/2013 | Burnell |
| 8,409,138 B2 | 4/2013 | James et al. |
| 8,409,141 B2 | 4/2013 | Johansen et al. |
| 8,491,530 B2 | 7/2013 | Maritan |
| 8,556,861 B2 | 10/2013 | Tsals |
| 8,696,628 B2 | 4/2014 | Grunhut |
| 8,932,264 B2 | 1/2015 | DeSalvo |
| 8,968,236 B2 * | 3/2015 | Jennings ............ A61M 5/2033 604/68 |
| 9,028,451 B2 | 5/2015 | Jennings |
| 9,248,245 B2 | 2/2016 | Ekman et al. |
| 9,314,574 B2 | 4/2016 | Roberts et al. |
| 9,358,346 B2 | 6/2016 | Beyeler |
| 9,592,350 B2 | 3/2017 | Roberts et al. |
| 9,675,757 B2 | 6/2017 | Harrison |
| 9,757,520 B2 | 9/2017 | Corrigan |
| 2001/0005781 A1 | 6/2001 | Bergens et al. |
| 2001/0021826 A1 | 9/2001 | Winkler |
| 2001/0021828 A1 | 9/2001 | Fischer et al. |
| 2001/0037087 A1 | 11/2001 | Knauer |
| 2001/0037089 A1 | 11/2001 | Domici, Jr. |
| 2001/0039394 A1 | 11/2001 | Terrence et al. |
| 2001/0049496 A1 | 12/2001 | Kirchhofer et al. |
| 2001/0051789 A1 | 12/2001 | Parsons |
| 2002/0032412 A1 | 3/2002 | Riemelmoser |
| 2002/0072709 A1 | 6/2002 | Sadowski et al. |
| 2002/0095120 A1 | 7/2002 | Larsen et al. |
| 2002/0151839 A1 | 10/2002 | Landau |
| 2002/0161334 A1 | 10/2002 | Castellano et al. |
| 2002/0165500 A1 | 11/2002 | Bechtold et al. |
| 2002/0173752 A1 | 11/2002 | Polzin |
| 2002/0183690 A1 | 12/2002 | Arnisolle |
| 2003/0036679 A1 | 2/2003 | Kortenbach |
| 2003/0036725 A1 | 2/2003 | Lavi et al. |
| 2003/0050609 A1 | 3/2003 | Sams |
| 2003/0060773 A1 | 3/2003 | Nguyen |
| 2003/0065286 A1 | 4/2003 | Landau |
| 2003/0078546 A1 | 4/2003 | Jensen |
| 2003/0088207 A1 | 5/2003 | Rogatchev et al. |
| 2003/0088216 A1 | 5/2003 | Py |
| 2003/0093030 A1 | 5/2003 | Landau |
| 2003/0093035 A1 | 5/2003 | Mohammed |
| 2003/0093036 A1 | 5/2003 | Crossman et al. |
| 2003/0105430 A1 | 6/2003 | Lavi et al. |
| 2003/0109833 A1 | 6/2003 | Sharpe |
| 2003/0120212 A1 | 6/2003 | Dedig et al. |
| 2003/0120222 A1 | 6/2003 | Vaillancourt |
| 2003/0121815 A1 | 7/2003 | Bergeron et al. |
| 2003/0135157 A1 | 7/2003 | Saulenas et al. |
| 2003/0181859 A1 | 9/2003 | Brunel |
| 2003/0184973 A1 | 10/2003 | Nagata et al. |
| 2003/0187405 A1 | 10/2003 | Gatti |
| 2003/0196928 A1 | 10/2003 | Parsons |
| 2003/0199814 A1 | 10/2003 | Parsons et al. |
| 2003/0208164 A1 | 11/2003 | Botich et al. |
| 2003/0212362 A1 | 11/2003 | Roser |
| 2003/0212370 A1 | 11/2003 | Barrelle |
| 2003/0212380 A1 | 11/2003 | Barrelle |
| 2003/0225368 A1 | 12/2003 | Landau et al. |
| 2003/0229308 A1 | 12/2003 | Tsals et al. |
| 2003/0233070 A1 | 12/2003 | De La Serna et al. |
| 2003/0236502 A1 | 12/2003 | De La Serna et al. |
| 2003/0236504 A1 | 12/2003 | Chen |
| 2004/0002684 A1 | 1/2004 | Lopez |
| 2004/0015134 A1 | 1/2004 | Lavi et al. |
| 2004/0019326 A1 | 1/2004 | Gilbert et al. |
| 2004/0024367 A1 | 2/2004 | Gilbert |
| 2004/0039336 A1 | 2/2004 | Amark et al. |
| 2004/0039366 A1 | 2/2004 | MacLeod |
| 2004/0069044 A1 | 4/2004 | Lavi et al. |
| 2004/0087897 A1 | 5/2004 | Hjertman |
| 2004/0094396 A1 | 5/2004 | Lee et al. |
| 2004/0102740 A1 | 5/2004 | Meloul |
| 2004/0111054 A1 | 6/2004 | Landau et al. |
| 2004/0111057 A1 | 6/2004 | Wilkinson |
| 2004/0133159 A1 | 7/2004 | Haider et al. |
| 2004/0138618 A1 | 7/2004 | Mazzoni |
| 2004/0143224 A1 | 7/2004 | Field et al. |
| 2004/0153033 A1 | 8/2004 | Mazzoni |
| 2004/0225262 A1 | 11/2004 | Fathallah et al. |
| 2004/0243065 A1 | 12/2004 | McConnell et al. |
| 2004/0254526 A1 | 12/2004 | Terrence et al. |
| 2005/0011780 A1 | 1/2005 | Simon et al. |
| 2005/0020979 A1 | 1/2005 | Westbye et al. |
| 2005/0020980 A1 | 1/2005 | Inoue et al. |
| 2005/0027255 A1 | 2/2005 | Lavi et al. |
| 2005/0033234 A1 | 2/2005 | Sadowski et al. |
| 2005/0035029 A1 | 2/2005 | Grob |
| 2005/0040716 A1 | 2/2005 | Schmid et al. |
| 2005/0049550 A1 | 3/2005 | Kirchhofer et al. |
| 2005/0049561 A1 | 3/2005 | Hommann et al. |
| 2005/0075608 A1 | 4/2005 | Holdgate et al. |
| 2005/0085776 A1 | 4/2005 | Hommann et al. |
| 2005/0090782 A1 | 4/2005 | Marshall et al. |
| 2005/0097238 A1 | 5/2005 | Oomori et al. |
| 2005/0101919 A1 | 5/2005 | Brunnberg |
| 2005/0113747 A1 | 5/2005 | Moir |
| 2005/0124940 A1 | 6/2005 | Martin et al. |
| 2005/0125019 A1 | 6/2005 | Kudna et al. |
| 2005/0137523 A1 | 6/2005 | Wyatt et al. |
| 2005/0165360 A1 | 7/2005 | Stamp |
| 2005/0168855 A1 | 8/2005 | Fanelli et al. |
| 2005/0203466 A1 | 9/2005 | Hommann et al. |
| 2005/0209554 A1 | 9/2005 | Landau |
| 2005/0215941 A1 | 9/2005 | Bernard et al. |
| 2005/0215951 A1 | 9/2005 | Saulenas et al. |
| 2005/0222539 A1 | 10/2005 | Gonzales et al. |
| 2005/0261633 A1 | 11/2005 | Khalaj |
| 2005/0261634 A1 | 11/2005 | Karlsson |
| 2005/0267403 A1 | 12/2005 | Landau et al. |
| 2005/0273054 A1 | 12/2005 | Asch |
| 2005/0273055 A1 | 12/2005 | Harrison et al. |
| 2005/0277885 A1 | 12/2005 | Scherer |
| 2005/0277886 A1 | 12/2005 | Hommann et al. |
| 2005/0277896 A1 | 12/2005 | Messerli et al. |
| 2005/0288633 A1 | 12/2005 | Jeffrey |
| 2006/0016835 A1 | 1/2006 | Perry |
| 2006/0030819 A1 | 2/2006 | Young et al. |
| 2006/0036216 A1 | 2/2006 | Rimlinger et al. |
| 2006/0036217 A1 | 2/2006 | Doyle |
| 2006/0069345 A1 | 3/2006 | Anderson et al. |
| 2006/0069348 A1 | 3/2006 | Parker et al. |
| 2006/0069350 A1 | 3/2006 | Buenger et al. |
| 2006/0079834 A1 | 4/2006 | Tennican et al. |
| 2006/0100588 A1 | 5/2006 | Brunnberg et al. |
| 2006/0106295 A1 | 5/2006 | Jais et al. |
| 2006/0161111 A1 | 7/2006 | Potter et al. |
| 2006/0178630 A1 | 8/2006 | Bostrom et al. |
| 2006/0178631 A1 | 8/2006 | Gillespie et al. |
| 2006/0178642 A1 | 8/2006 | Gillespie et al. |
| 2006/0184119 A1 | 8/2006 | Remde et al. |
| 2006/0184137 A1 | 8/2006 | Reynolds |
| 2006/0189938 A1 | 8/2006 | Hommann et al. |
| 2006/0200093 A1 | 9/2006 | Lopez |
| 2006/0206060 A1 | 9/2006 | Lopez |
| 2006/0224124 A1 | 10/2006 | Scherer |
| 2006/0229572 A1 | 10/2006 | Lopez |
| 2006/0258986 A1 | 11/2006 | Hunter et al. |
| 2006/0258990 A1 | 11/2006 | Weber |
| 2006/0270986 A1 | 11/2006 | Hommann et al. |
| 2007/0021716 A1 | 1/2007 | Hansen |
| 2007/0027430 A1 | 2/2007 | Hommann |
| 2007/0032775 A1 | 2/2007 | Niedospial et al. |
| 2007/0066939 A1 | 3/2007 | Krulevitch et al. |
| 2007/0078382 A1 | 4/2007 | Hommann et al. |
| 2007/0078428 A1 | 4/2007 | Reynolds et al. |
| 2007/0118094 A1 | 5/2007 | Bingham et al. |
| 2007/0135767 A1 | 6/2007 | Gillespie, II et al. |
| 2007/0142787 A1 | 6/2007 | Scherer |

(56) References Cited

U.S. PATENT DOCUMENTS

| | | |
|---|---|---|
| 2007/0150842 A1* | 6/2007 | Chaudhri ............... H04M 1/67 715/863 |
| 2007/0156091 A1 | 7/2007 | Fathallah et al. |
| 2007/0156112 A1 | 7/2007 | Walsh |
| 2007/0208296 A1 | 9/2007 | Paproski et al. |
| 2007/0244456 A1 | 10/2007 | Fangrow |
| 2007/0244457 A1 | 10/2007 | Fangrow |
| 2007/0244458 A1 | 10/2007 | Fangrow |
| 2007/0244459 A1 | 10/2007 | Fangrow |
| 2007/0244460 A1 | 10/2007 | Fangrow |
| 2007/0244461 A1 | 10/2007 | Fangrow |
| 2007/0244462 A1 | 10/2007 | Fangrow |
| 2007/0244463 A1 | 10/2007 | Warren et al. |
| 2007/0244464 A1 | 10/2007 | Fangrow et al. |
| 2007/0244465 A1 | 10/2007 | Fangrow |
| 2007/0244466 A1 | 10/2007 | Fangrow |
| 2008/0033395 A1 | 2/2008 | Alchas |
| 2008/0071225 A1 | 3/2008 | Hommann et al. |
| 2008/0154192 A1 | 6/2008 | Schraga |
| 2008/0161770 A1 | 7/2008 | Fangrow |
| 2008/0172001 A1 | 7/2008 | Reynolds et al. |
| 2008/0172024 A1 | 7/2008 | Yow |
| 2008/0213590 A1 | 9/2008 | Greiner et al. |
| 2008/0249462 A1* | 10/2008 | Smith ................. A61M 31/00 604/60 |
| 2008/0249498 A1 | 10/2008 | Fangrow |
| 2008/0262427 A1 | 10/2008 | Hommann |
| 2008/0269680 A1 | 10/2008 | Ibranyan et al. |
| 2008/0306443 A1 | 12/2008 | Neer et al. |
| 2008/0312592 A1 | 12/2008 | Barrow-Williams et al. |
| 2008/0312602 A1 | 12/2008 | Barrow-Williams et al. |
| 2008/0312606 A1 | 12/2008 | Harrison et al. |
| 2009/0036764 A1 | 2/2009 | Rivas et al. |
| 2009/0054849 A1 | 2/2009 | Burnell et al. |
| 2009/0088688 A1 | 4/2009 | Donald et al. |
| 2009/0149812 A1 | 6/2009 | MacAulay |
| 2009/0209554 A1 | 8/2009 | Boyd et al. |
| 2009/0234297 A1 | 9/2009 | Jennings |
| 2010/0016793 A1 | 1/2010 | Jennings et al. |
| 2010/0036319 A1 | 2/2010 | Drake et al. |
| 2010/0049125 A1 | 2/2010 | James et al. |
| 2010/0063444 A1 | 3/2010 | Wikner |
| 2010/0234811 A1 | 9/2010 | Schubert et al. |
| 2010/0286714 A1 | 11/2010 | Gyrn et al. |
| 2011/0092954 A1 | 4/2011 | Jennings |
| 2011/0098647 A1 | 4/2011 | Jennings |
| 2011/0098655 A1 | 4/2011 | Jennings et al. |
| 2011/0098656 A1 | 4/2011 | Burnell et al. |
| 2011/0130743 A1 | 6/2011 | Jennings et al. |
| 2011/0144594 A1 | 6/2011 | Sund et al. |
| 2011/0172640 A1* | 7/2011 | Cronenberg ...... A61M 5/31576 604/506 |
| 2011/0245761 A1* | 10/2011 | Jennings ............. A61M 5/2033 604/68 |
| 2011/0282278 A1 | 11/2011 | Stamp et al. |
| 2012/0046615 A1 | 2/2012 | Iwase et al. |
| 2012/0232491 A1 | 9/2012 | Jennings |
| 2012/0283698 A1 | 11/2012 | Millerd |
| 2012/0323177 A1 | 12/2012 | Adams et al. |
| 2013/0046246 A1 | 2/2013 | Boyd et al. |
| 2013/0060232 A1 | 3/2013 | Adlon et al. |
| 2013/0096512 A1 | 4/2013 | Ekman et al. |
| 2013/0125441 A1* | 5/2013 | Westwood ............. F41A 17/02 42/70.05 |
| 2013/0150801 A1 | 6/2013 | Barrow-Williams et al. |
| 2013/0267898 A1 | 10/2013 | Hourmand et al. |
| 2013/0310759 A1 | 11/2013 | Barrow-Williams et al. |
| 2013/0317446 A1 | 11/2013 | Hourmand et al. |
| 2013/0331794 A1 | 12/2013 | Ekman et al. |
| 2013/0338601 A1 | 12/2013 | Cowe |
| 2013/0345643 A1 | 12/2013 | Hourmand et al. |
| 2014/0221974 A1 | 8/2014 | Bechmann et al. |
| 2014/0257185 A1 | 9/2014 | Bechmann et al. |
| 2014/0257193 A1 | 9/2014 | Bostrom et al. |
| 2015/0025458 A1 | 1/2015 | Heald et al. |
| 2015/0051551 A1 | 2/2015 | Hirschel et al. |
| 2015/0190590 A1* | 7/2015 | Richter .................. A61M 5/20 604/111 |
| 2018/0312590 A1 | 11/2018 | Cogswell et al. |

FOREIGN PATENT DOCUMENTS

| | | |
|---|---|---|
| CH | 703993 | 3/2012 |
| CN | 2059579 U | 7/1990 |
| CN | 1190599 A | 8/1998 |
| CN | 1420794 A | 5/2003 |
| CN | 1541121 A | 10/2004 |
| CN | 1550240 A | 12/2004 |
| CN | 101014379 A | 8/2007 |
| CN | 101068585 A | 11/2007 |
| DE | 387465 | 1/1924 |
| DE | 902776 C | 1/1954 |
| DE | 229932 A1 | 11/1985 |
| DE | 3604826 A1 | 10/1986 |
| DE | 4428467 A1 | 2/1996 |
| DE | 29513214 U1 | 2/1997 |
| DE | 19603707 A1 | 8/1997 |
| DE | 69506521 T2 | 6/1999 |
| DE | 10137962 A1 | 2/2003 |
| DE | 10207276 A1 | 9/2003 |
| DE | 20311996 U1 | 11/2003 |
| EP | 0096314 A2 | 12/1983 |
| EP | 0144625 A2 | 6/1985 |
| EP | 0240787 A2 | 10/1987 |
| EP | 0338806 A2 | 10/1989 |
| EP | 0515473 B1 | 12/1992 |
| EP | 0518416 A1 | 12/1992 |
| EP | 0331452 B1 | 8/1993 |
| EP | 0585626 A1 | 3/1994 |
| EP | 0389938 B1 | 5/1994 |
| EP | 0516473 B1 | 2/1996 |
| EP | 0111724 B1 | 2/1998 |
| EP | 0482677 B1 | 4/1998 |
| EP | 0602883 B1 | 7/1998 |
| EP | 0857491 A1 | 8/1998 |
| EP | 0824922 B1 | 4/2002 |
| EP | 1260241 A1 | 11/2002 |
| EP | 0824923 B1 | 7/2003 |
| EP | 1228777 B1 | 10/2003 |
| EP | 0991441 B1 | 12/2003 |
| EP | 1166809 B1 | 3/2004 |
| EP | 0666084 B1 | 4/2004 |
| EP | 0941133 B1 | 4/2004 |
| EP | 1124601 B1 | 12/2004 |
| EP | 1364667 B1 | 4/2005 |
| EP | 1208858 B1 | 6/2006 |
| EP | 1586341 B1 | 1/2008 |
| EP | 2023980 A1 | 2/2009 |
| EP | 2129414 B1 | 12/2009 |
| EP | 1755706 B1 | 3/2010 |
| EP | 1928523 B1 | 7/2010 |
| EP | 1518575 B1 | 11/2010 |
| EP | 1932558 B1 | 6/2011 |
| EP | 1755710 B1 | 3/2012 |
| EP | 2468330 A1 | 6/2012 |
| EP | 2340863 B1 | 11/2013 |
| EP | 2620174 B1 | 5/2014 |
| EP | 2675509 B1 | 4/2015 |
| EP | 2705861 B1 | 4/2015 |
| EP | 2319560 | 5/2015 |
| EP | 2414003 B1 | 5/2015 |
| EP | 2464401 B1 | 5/2015 |
| EP | 2493531 B1 | 7/2015 |
| EP | 2705862 B1 | 7/2015 |
| EP | 2268342 | 9/2015 |
| EP | 2588173 B1 | 10/2015 |
| EP | 2470241 B1 | 11/2015 |
| EP | 2768556 B1 | 12/2015 |
| EP | 2355872 B1 | 1/2016 |
| EP | 2720738 B1 | 1/2016 |
| EP | 1412000 B1 | 2/2016 |
| EP | 2671606 B1 | 3/2016 |
| EP | 2760507 B1 | 4/2016 |

(56) References Cited

FOREIGN PATENT DOCUMENTS

| | | |
|---|---|---|
| FR | 1014881 A | 8/1952 |
| FR | 1169935 A | 1/1959 |
| FR | 1538565 A | 9/1968 |
| FR | 2506161 A1 | 11/1982 |
| FR | 2629706 A | 10/1989 |
| FR | 2654938 A1 | 5/1991 |
| FR | 2665079 A1 | 1/1992 |
| FR | 2717086 A1 | 9/1995 |
| FR | 2741810 A1 | 6/1997 |
| FR | 2805868 A1 | 9/2001 |
| FR | 2830765 A1 | 4/2003 |
| FR | 2861310 A1 | 4/2005 |
| GB | 143084 A | 5/1920 |
| GB | 412054 A | 6/1934 |
| GB | 728248 A | 4/1955 |
| GB | 909898 A | 11/1962 |
| GB | 1263355 A | 2/1972 |
| GB | 1311937 A | 3/1973 |
| GB | 1514725 A | 6/1978 |
| GB | 2388033 A | 11/2003 |
| GB | 2396298 A | 6/2004 |
| GB | 2396816 A | 7/2004 |
| GB | 2397767 A | 8/2004 |
| GB | 2404338 A | 2/2005 |
| GB | 2414398 A | 11/2005 |
| GB | 2414399 A | 11/2005 |
| GB | 2414400 A | 11/2005 |
| GB | 2414401 A | 11/2005 |
| GB | 2414402 A | 11/2005 |
| GB | 2414403 A | 11/2005 |
| GB | 2424835 A | 10/2006 |
| GB | 2424836 A | 10/2006 |
| GB | 2424837 A | 10/2006 |
| GB | 2424838 A | 10/2006 |
| GB | 2425062 A | 10/2006 |
| GB | 2433035 A | 6/2007 |
| GB | 2437922 A | 11/2007 |
| GB | 2438591 A | 12/2007 |
| GB | 2443606 A | 5/2008 |
| GB | 2445090 A | 6/2008 |
| GB | 2446778 A | 8/2008 |
| GB | 2451663 A | 2/2009 |
| GB | 2451665 A | 2/2009 |
| GB | 2452286 A | 3/2009 |
| GB | 2515041 B | 12/2014 |
| JP | 30-001091 | 1/1930 |
| JP | 49-77487 | 7/1974 |
| JP | 49-021036 | 6/1979 |
| JP | 54-087694 | 1/1982 |
| JP | 59-115053 A | 7/1984 |
| JP | 2-185261 A | 7/1990 |
| JP | 2-502971 T | 9/1990 |
| JP | H 02-299660 A | 12/1990 |
| JP | 03-129156 | 12/1991 |
| JP | 11-501549 T | 2/1992 |
| JP | 5-161712 A | 6/1993 |
| JP | 6-209996 A | 8/1994 |
| JP | 6-508773 T | 10/1994 |
| JP | 6-327770 A | 11/1994 |
| JP | H 07-116224 A | 5/1995 |
| JP | 7-213610 A | 8/1995 |
| JP | 7-222799 A | 8/1995 |
| JP | 8-502180 T | 3/1996 |
| JP | 8-504354 T | 5/1996 |
| JP | 9-225029 A | 9/1997 |
| JP | 10-504474 T | 5/1998 |
| JP | 10-507935 A | 8/1998 |
| JP | 11-503637 T | 3/1999 |
| JP | 11-504536 T | 4/1999 |
| JP | 11-164887 T | 6/1999 |
| JP | 11-512332 T | 10/1999 |
| JP | 2000-126293 A | 5/2000 |
| JP | 2000-510021 T | 8/2000 |
| JP | 2001-046498 A | 2/2001 |
| JP | 2001-065786 | 3/2001 |
| JP | 2001-212237 A | 8/2001 |
| JP | 2002-500933 T | 1/2002 |
| JP | 2002-502296 A | 1/2002 |
| JP | 2002-095749 A | 4/2002 |
| JP | 2002-513547 T | 5/2002 |
| JP | 2002-526175 A | 8/2002 |
| JP | 2002-528182 T | 9/2002 |
| JP | 2002-532161 T | 10/2002 |
| JP | 2003-511105 T | 3/2003 |
| JP | 2003-154005 | 5/2003 |
| JP | 2003-284776 | 10/2003 |
| JP | 2003-532500 T | 11/2003 |
| JP | 2003-533288 A | 11/2003 |
| JP | 2004-033737 A | 2/2004 |
| JP | 2004-533282 T | 11/2004 |
| JP | 2004-537376 A | 12/2004 |
| JP | 2005-508214 A | 3/2005 |
| JP | 2005-177503 A | 7/2005 |
| JP | 2005-534433 | 11/2005 |
| JP | 2006-223858 A | 8/2006 |
| JP | 2007-207611 A | 8/2007 |
| JP | 2008-284177 A | 11/2008 |
| JP | 2008-295590 | 12/2008 |
| JP | 2008-543500 | 12/2008 |
| JP | 2012-503995 | 2/2012 |
| JP | 2013-529527 | 7/2013 |
| NZ | 335985 A | 4/2001 |
| NZ | 573171 A | 11/2010 |
| NZ | 573350 A | 12/2010 |
| WO | WO 87/07843 A1 | 12/1987 |
| WO | WO 88/08725 A1 | 11/1988 |
| WO | WO 1988/10129 A1 | 12/1988 |
| WO | WO 92/19296 A | 11/1992 |
| WO | WO 1993/02186 A1 | 2/1993 |
| WO | WO 93/21986 A2 | 11/1993 |
| WO | WO 1993/23098 A1 | 11/1993 |
| WO | WO 1994/04207 A1 | 3/1994 |
| WO | WO 94/07554 A1 | 4/1994 |
| WO | WO 94/11041 A1 | 5/1994 |
| WO | WO 94/13342 A1 | 6/1994 |
| WO | WO 94/013343 | 6/1994 |
| WO | WO 94/21316 A1 | 9/1994 |
| WO | WO 94/22511 A1 | 10/1994 |
| WO | WO 95/04562 A1 | 2/1995 |
| WO | WO 95/31235 A1 | 11/1995 |
| WO | WO 1995/29720 A1 | 11/1995 |
| WO | WO 1995/35126 A1 | 11/1995 |
| WO | WO 95/35126 A1 | 12/1995 |
| WO | WO 96/30065 A1 | 10/1996 |
| WO | WO 97/10865 A1 | 3/1997 |
| WO | WO 1997/13538 A1 | 4/1997 |
| WO | WO 97/48430 A1 | 12/1997 |
| WO | WO 98/11927 A1 | 3/1998 |
| WO | WO 99/03529 A2 | 1/1999 |
| WO | WO 99/10030 A2 | 3/1999 |
| WO | WO 99/22789 A1 | 5/1999 |
| WO | WO 99/37343 A | 7/1999 |
| WO | WO 99/53979 A1 | 10/1999 |
| WO | WO 1999/59658 A1 | 11/1999 |
| WO | WO 00/06227 A1 | 2/2000 |
| WO | WO 00/07539 A1 | 2/2000 |
| WO | WO 00/13723 A2 | 3/2000 |
| WO | WO 00/24441 A1 | 5/2000 |
| WO | WO 00/35516 A1 | 6/2000 |
| WO | WO 00/50107 A1 | 8/2000 |
| WO | WO 00/61209 A1 | 10/2000 |
| WO | WO 00/64515 A1 | 11/2000 |
| WO | WO 00/69488 A2 | 11/2000 |
| WO | WO 01/05456 A1 | 1/2001 |
| WO | WO 01/49347 A1 | 7/2001 |
| WO | WO 01/60435 A1 | 8/2001 |
| WO | WO 01/76666 A1 | 10/2001 |
| WO | WO 01/077384 A2 | 10/2001 |
| WO | WO 01/87384 A1 | 11/2001 |
| WO | WO 02/11799 A1 | 2/2002 |
| WO | WO 02/47746 A1 | 6/2002 |
| WO | WO 02/056947 A1 | 7/2002 |
| WO | WO 02/074361 A2 | 9/2002 |
| WO | WO 03/013632 A2 | 2/2003 |

(56) References Cited

FOREIGN PATENT DOCUMENTS

| | | |
|---|---|---|
| WO | WO 03/015846 A2 | 2/2003 |
| WO | WO 03/015853 A1 | 2/2003 |
| WO | WO 03/039633 A2 | 5/2003 |
| WO | WO 03/041768 A | 5/2003 |
| WO | WO 03/047663 A2 | 6/2003 |
| WO | WO 03/051434 A2 | 6/2003 |
| WO | WO 03/066141 A1 | 8/2003 |
| WO | WO 03/092771 A1 | 11/2003 |
| WO | WO 03/097133 A1 | 11/2003 |
| WO | WO 03/099358 A2 | 12/2003 |
| WO | WO 04/007554 A1 | 1/2004 |
| WO | WO 04/011065 A1 | 2/2004 |
| WO | WO 2004/030732 A2 | 4/2004 |
| WO | WO 2004/035117 A2 | 4/2004 |
| WO | WO 2004/047890 A1 | 6/2004 |
| WO | WO 2004/047891 A1 | 6/2004 |
| WO | WO 2004/047892 A | 6/2004 |
| WO | WO 2004/054644 A1 | 7/2004 |
| WO | WO 2004/054645 A3 | 7/2004 |
| WO | WO 2004/087242 | 10/2004 |
| WO | WO 2004/087242 A1 | 10/2004 |
| WO | WO 2004/101025 A2 | 11/2004 |
| WO | WO 2004/108194 A1 | 12/2004 |
| WO | WO 2005/004961 A1 | 1/2005 |
| WO | WO 2005/009515 A1 | 2/2005 |
| WO | WO 2005/023341 A1 | 3/2005 |
| WO | WO 2005/025636 A2 | 3/2005 |
| WO | WO 2005/030301 A1 | 4/2005 |
| WO | WO 2005/035028 A1 | 4/2005 |
| WO | WO 2005/044345 A | 5/2005 |
| WO | WO 2005/044347 A1 | 5/2005 |
| WO | WO 2005/044348 | 5/2005 |
| WO | WO 2005/056077 | 6/2005 |
| WO | WO 2005/058393 A2 | 6/2005 |
| WO | WO 2005/058396 A1 | 6/2005 |
| WO | WO 2005/070481 A1 | 8/2005 |
| WO | WO 2005/082438 A1 | 9/2005 |
| WO | WO 2005/097238 A3 | 10/2005 |
| WO | WO 2005/105014 A2 | 11/2005 |
| WO | WO 2005/115507 A1 | 12/2005 |
| WO | WO 2005/115508 A1 | 12/2005 |
| WO | WO 2005/115509 A1 | 12/2005 |
| WO | WO 2005/115510 A1 | 12/2005 |
| WO | WO 2005/115512 A1 | 12/2005 |
| WO | WO 2005/115513 A1 | 12/2005 |
| WO | WO 2005/115514 A1 | 12/2005 |
| WO | WO 2005/115516 A1 | 12/2005 |
| WO | WO 2005/120607 A2 | 12/2005 |
| WO | WO 2006/008086 A1 | 1/2006 |
| WO | WO 2006/044236 A2 | 4/2006 |
| WO | WO 2006/050304 A1 | 5/2006 |
| WO | WO 2006/062788 A2 | 6/2006 |
| WO | WO 2006/063015 A2 | 6/2006 |
| WO | WO 2006/063124 A2 | 6/2006 |
| WO | WO 2006/088513 A1 | 8/2006 |
| WO | WO 2006/088630 A2 | 8/2006 |
| WO | WO 2006/099441 A2 | 9/2006 |
| WO | WO 2006/106290 A1 | 10/2006 |
| WO | WO 2006/106291 A1 | 10/2006 |
| WO | WO 2006/106292 A1 | 10/2006 |
| WO | WO 2006/106293 A1 | 10/2006 |
| WO | WO 2006/106294 A | 10/2006 |
| WO | WO 2006/106295 A1 | 10/2006 |
| WO | WO 2006/118616 A1 | 11/2006 |
| WO | WO 2006/129196 A1 | 12/2006 |
| WO | WO 2007/027204 A2 | 3/2007 |
| WO | WO 2007/036676 A1 | 4/2007 |
| WO | WO 2007/047200 A1 | 4/2007 |
| WO | WO 2007/051330 A1 | 5/2007 |
| WO | WO 2007/066152 A | 6/2007 |
| WO | WO 2007/066152 A2 | 6/2007 |
| WO | WO 2007/122193 A1 | 11/2007 |
| WO | WO 2007/129324 A2 | 11/2007 |
| WO | WO 2007/131013 A | 11/2007 |
| WO | WO 2007/138299 A1 | 12/2007 |
| WO | WO 2008/047372 A2 | 4/2008 |
| WO | WO 2008/059233 A1 | 5/2008 |
| WO | WO 2008/075033 A | 6/2008 |
| WO | WO 2008/093063 A2 | 8/2008 |
| WO | WO 2010/023303 A1 | 3/2010 |
| WO | WO 2010/056712 | 5/2010 |
| WO | WO 2011/117283 | 9/2011 |
| WO | WO 2012/000835 A1 | 1/2012 |
| WO | WO 2012/059517 | 5/2012 |
| WO | WO 2012/093071 | 7/2012 |
| WO | WO 2012/140088 | 10/2012 |
| WO | WO 2012/155035 | 11/2012 |
| WO | WO 2013/070715 | 5/2013 |

OTHER PUBLICATIONS

Cam Design and Manufacture; Preben W. Jensen; Industrial Press; New York; 1965; Chapter 1.

Definition of a cam taken from www.wikipedia.com, Feb. 7, 2012.

Farm gate latch image Website showing gate latches from Mar. 6, 2004, http://dictionary.cambridge.org/dictionary/british/latch.

Engineering Tolerance, definition, Aug. 15, 2013; http://en.wikipedia.org/wiki/Engineering_tolerance.

Witness statement by Mr. Jeremy Marshal, Head of Technology Development & CI of the opponent, Dec. 2, 2011.

Patient instruction leaflet Glaxo Mode d'emploi (FR); Referred to in Statement of Jeremy Marshall, Dec. 2, 2011.

Assembly instructions, process flow diagrams for AJ1200CE129 and AJ1200CA00 together with drawings for AJ501 all dated differently; starting in 1993 and the latest dates referring to 2002, Referred to in Statement of Jeremy Marshall, Dec. 2, 2011.

Discussion session at the 5th International Nurses' Workshop on Multiple Sclerosis.

Article from diabetes health, Jan. 2, 1997.

Parts list AJ503 Auto injector—Glaxo Jul. 29, 1992 (change 92-7-45)/ 18.10.1993 with drawings dated between 1986 and 1991.

Photos of a sample, Referred to in Statement of Jeremy Marshall, Dec. 2, 2011.

Company's sales ledger for the period of Nov. 1991-May 1993.

510(k) pre-market notification Apr. 19, 1990.

Fax dated Jul. 21, 1995 Imigran injection launch data.

Patient instruction leaflet, Imigran, Referred to in Statement of Jeremy Marshall, Dec. 2, 2011.

Patient instruction leaflet Glaxo Neurologie (NL), Referred to in Statement of Jeremy Marshall, Dec. 2, 2011.

Parts list AJ501 stamped Jul. 8, 2002.

Patient instruction leaflet Imigran (EN), Referred to in Statement of Jeremy Marshall, Dec. 2, 2011.

Detailed view of the retainer component AJ613 dated Jun. 15, 1993 last amended Aug. 11, 1995.

Production drawing Nov. 18, 2003, Autoject2 fixed needle AJ-0530-00-00-33.

Bill of material amendments log, Dec. 2, 2011.

Internet archive pages dated Apr. 12, 1999_1.

Internet archive pages dated Apr. 12, 1999_2.

Invoices of sales Dec. 12, 2005 Autoject 2—Product code AJ1300EA000 and invoice of sales Mar. 21, 2006 Autoject 2—Product code AJ1311EA000.

Hospital price list Mar. 1990 and pharmacy trade price list Mar. 1994 losing an Autoinjector AJ1200.

Production record of Feb. 15, 2001 referring to device part AJ501 and a packaged part No. AJ1200CA00, dated Feb. 15, 2001.

Production record, dated raised Feb. 15, 2001.

Parts list for AJ501, Referred to in Statement of Jeremy Marshall, Dec. 2, 2011.

General assembly drawing issued Feb. 5, 1986, last amended Sep. 2, 1994.

Extracts from the company's sales ledger, Referred to in Statement of Jeremy Marshall, Dec. 2, 2011.

Extract from a medical shop catalogue, Referred to in Statement of Jeremy Marshall, Dec. 2, 2011.

Mechanical Engineer's Handbook; Dan B. Marghitu, J. David Irwin; Academic Press, Burlington, 2001.

(56) References Cited

OTHER PUBLICATIONS

Non-patent literature ISO 11040-4:1996('E').
European Pharmacopeia, 2002, p. 282-283.
"Starlock Fasteners": filed at the EPO by way of the opponent's letter of Apr. 3, 2013 and said to be retrieved from the website www.bakfin.com around that time.
Worksheet referred to in document A21; V. Ryan, 2002-2009; from www.technology student.com.
Dictionary definition of a latch; http://dictionary.cambridge.org/dictionary/british/latch, Oct. 12, 2014.
"Farm Gate Latch Image": filed at the EPO by way of the opponent's letter of Oct. 31, 2014.
GA drawing dated Oct. 6, 1994 several times amended.
Article Apr. 27, 2002 5th International Nurses' Workshop on Multiple Sclerosis.
International Search Report dated Jul. 9, 2004; International Application No. PCT/GB03/05494.
International Search Report dated Sep. 5, 2005; International Application No. PCT/GB2005/002117.
International Search Report dated May 30, 2006; International Application No. PCT/GB2005/003725.
International Search Report dated Sep. 9, 2005; International Application No. PCT/GB2005/002126.
International Search Report dated Sep. 5, 2005; International Application No. PCT/GB2005/002131.
International Search Report dated Sep. 9, 2005; International Application No. PCT/GB2005/002120.
International Search Report dated Sep. 5, 2005; International Application No. PCT/GB2005/002137.
International Search Report dated Sep. 6, 2005; International Application No. PCT/GB2005/002108.
International Search Report dated Sep. 5, 2005; International Application No. PCT/GB2005/002105.
International Search Report dated Sep. 5, 2005; International Application No. PCT/GB2005/002116.
International Search Report dated Sep. 5, 2005; International Application No. PCT/GB2005/002128.
International Search Report dated May 23, 2006; International Application No. PCT/GB2006/001017.
International Search Report dated May 29, 2006; International Application No. PCT/GB2006/001018.
International Search Report dated Jun. 2, 2006; International Application No. PCT/GB2006/001030.
International Search Report dated Jun. 1, 2006; International Application No. PCT/GB2006/001029.
International Search Report dated Sep. 9, 2005 International Application No. PCT/GB2005/002135.
International Search Report dated May 30, 2006; International Application No. PCT/GB2006/001031.
International Search Report dated Oct. 9, 2007; International Application No. PCT/GB2006/001023.
International Search Report dated Feb. 27, 2007; International Application No. PCT/IB2006/002792.
International Search Report dated Aug. 22, 2007; International Application No. PCT/GB2007/001992.
International Search Report dated Sep. 4, 2007; International Application No. PCT/GB2007/002002.
International Search Report dated Aug. 22, 2007; International Application No. PCT/GB2007/001973.
International Search Report dated Feb. 26, 2008; International Application No. PCT/GB2007/004335.
International Search Report dated Sep. 13, 2007; International Application No. PCT/GB2007/001999.
International Search Report dated Aug. 28, 2007; International Application No. PCT/GB2007/001969.
International Search Report dated Oct. 10, 2008; International Application No. PCT/GB2008/002578.
International Search Report dated Oct. 14, 2008; International Application No. PCT/GB2008/002580.
International Search Report dated Nov. 27, 2008; International Application No. PCT/GB2008/002579.
International Search Report dated Oct. 10, 2008; International Application No. PCT/GB2008/002573.
International Search Report dated Oct. 10, 2008; International Application No. PCT/GB2008/002583.
International Search Report dated Sep. 30, 2009; International Application No. PCT/GB2009/001447.
International Search Report dated Oct. 2, 2009; International Application No. PCT/GB2009/001448.
International Search Report dated Oct. 5, 2009; International Application No. PCT/GB2009/001451.
International Search Report dated Oct. 6, 2009; International Application No. PCT/GB2009/001453.
International Search Report dated Oct. 5, 2009; International Application No. PCT/GB2009/001445.
International Search Report dated Jan. 22, 2010; International Application No. PCT/GB2009/001446.
International Search Report dated Jan. 12, 2008; International Application No. PCT/GB2008/002475.
International Search Report dated Sep. 4, 2003; International Application No. PCT/GB03/01946.
International Search Report dated Sep. 8, 2014; International Application No. PCT/EP2014/062163.
International Search Report dated Sep. 8, 2014; International Application No. PCT/EP2014/062166.
International Search Report dated Sep. 17, 2014; International Application No. PCT/EP2014/062167.
International Search Report dated Jan. 29, 2015; International Application No. PCT/EP2014/062167.
International Search Report dated Sep. 9, 2014; International Application No. PCT/EP2014/062168.
International Search Report dated Sep. 8, 2014; International Application No. PCT/EP2014/062162.
International Search Report dated Sep. 16, 2014; International Application No. PCT/EP2014/062160.

* cited by examiner

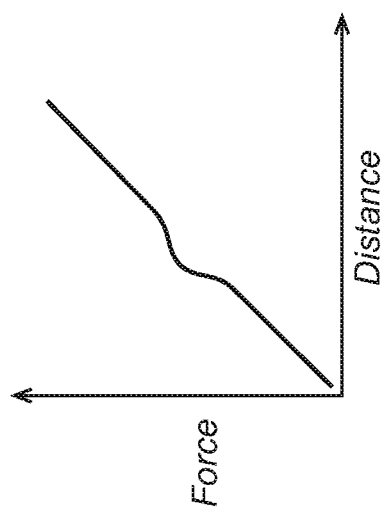
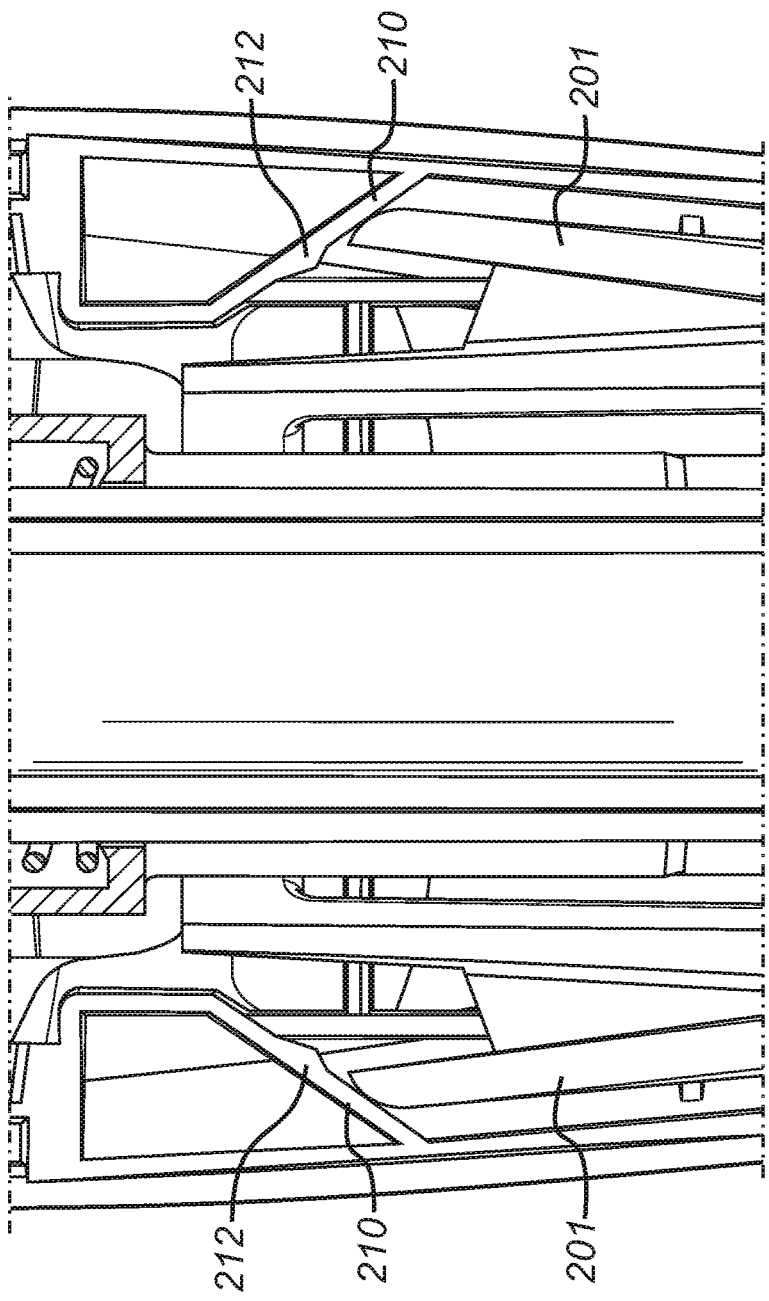

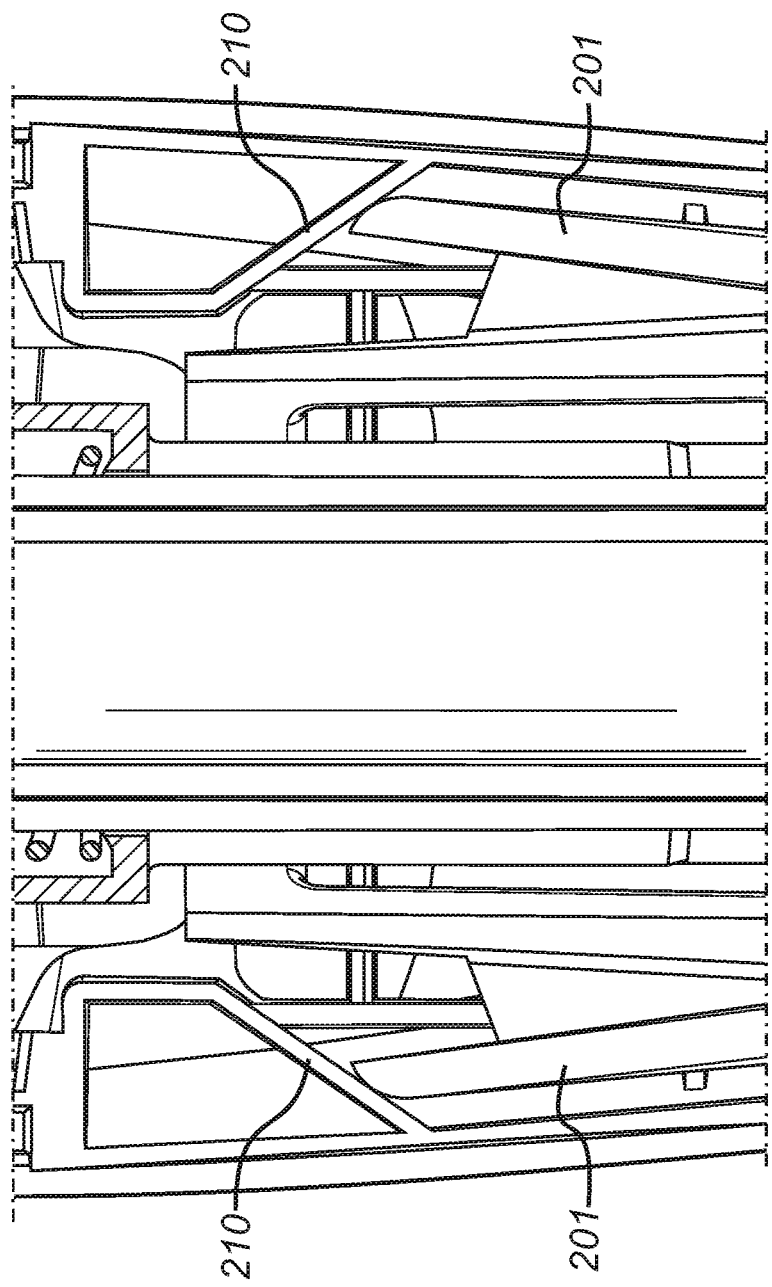
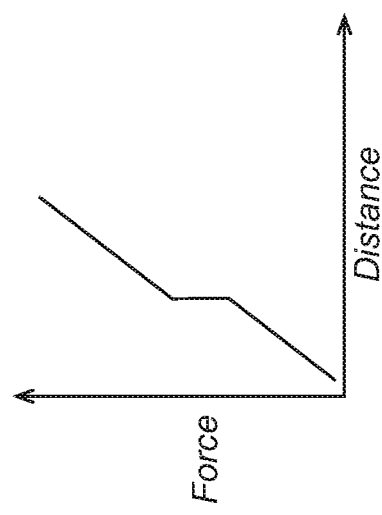

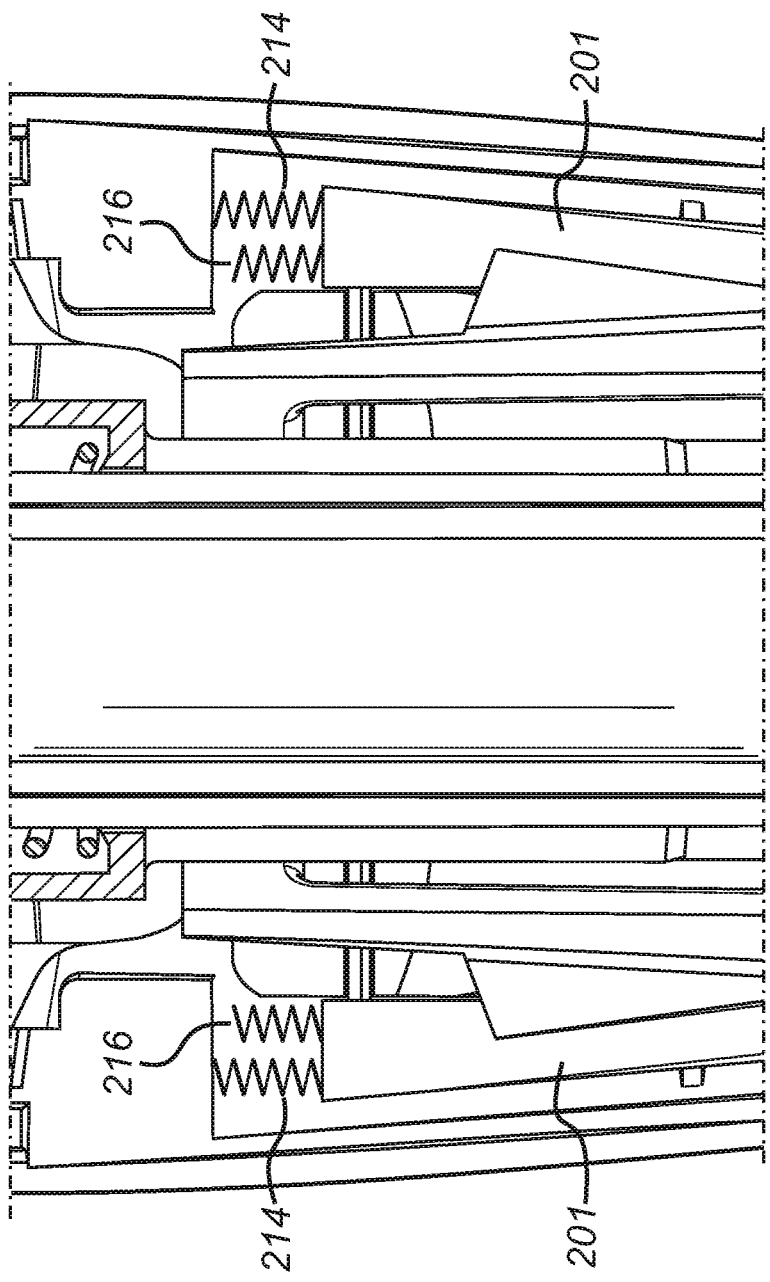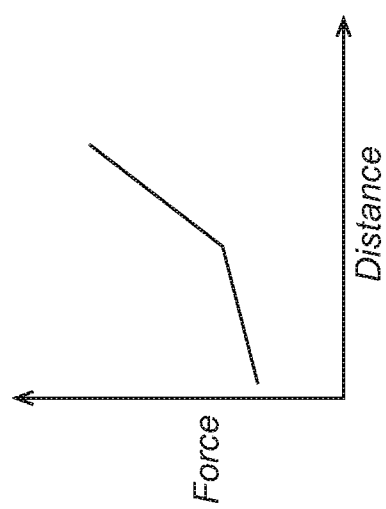

INJECTION DEVICE

FIELD OF THE INVENTION

The present invention relates to an injection device for delivering an injection, as well as an injection kit and a method of operating the injection device.

BACKGROUND OF THE INVENTION

Some conventional injection devices incorporate some form of impediment so as to selectively impede, or prevent, the delivery of an injection from the injection device. In such devices the injection can only be carried out when the user has moved the impediment out of its impeding position. This reduces the possibility of inadvertently delivering an injection from the injection device since any attempt to deliver the injection when the impediment is in its impeding position will not be successful. In other words, the injection device can be placed in a locked state. In order to successfully deliver an injection, the user must carry out the action to move the impediment, and so take the injection device out of its locked state, and then subsequently perform the action required for injection delivery.

Such an injection device is described in WO2006/106294. This injection device has an impediment in the form of a protrusion that, when in its impeding position, restricts the motion of the trigger that is required to commence the injection delivery. The impediment can be moved to a position where it does not restrict the motion of the trigger by moving a sliding sleeve into the housing of the injection device.

It has been found that users of injection devices, such as those described in WO2006/106294, struggle to discern when the impediment has been sufficiently moved in order to allow activation of the device. This can be very frustrating for users, since they may make numerous unsuccessful attempts at activating the injection as they are unaware that the impediment remains in its impeding position. Further, the frustrated user may attempt to force the injection device, i.e. by applying excessive pressure to the trigger, and so damage the injection mechanism.

There is therefore a need to provide an injection device that provides an intuitive feedback to the user to indicate the progress of the injection device from a locked state to a state in which the injection may be carried out. The present invention addresses such a problem.

SUMMARY OF THE INVENTION

A first aspect of the present invention provides an injection device for delivering an injection comprising a housing having a longitudinal axis, a proximal end and a distal end, the housing being arranged such that the injection is delivered from its distal end; and a release mechanism comprising an impediment, the release mechanism being movable between a first position, in which the impediment is in an impeding position so as to impede the delivery of the injection, and a second position, in which the impediment is in a non-impeding position so as to not impede the delivery of the injection, wherein the force required to move the release mechanism from the first position to the second position varies with the distance moved by the release mechanism, the variation in the force required with distance being represented by a force profile, which is non-linear.

In a second aspect, the present invention provides an injection device for delivering an injection comprising a housing having a longitudinal axis, a proximal end and a distal end, the housing being arranged such that the injection is delivered from its distal end; and a release mechanism comprising an impediment, the release mechanism being moveable between a first position, in which the impediment is in an impeding position so as to impede the delivery of the injection, and a second position, in which the impediment is in a non-impeding position so as to not impede the delivery of the injection, wherein the injection device produces an audible signal when the release mechanism is moved from the first position to the second position.

Hence, the injection device can be selectively placed in a locked state, where an impediment impedes, or prevents, the delivery of the injection from the injection device, which reduces the risk of inadvertently delivering an injection. The injection device can also be selectively placed in an unlocked state, where the impediment no longer impedes, or prevents, the delivery of the injection from the injection device, allowing the injection to be administered.

The injection device is preferably an auto-injector. Auto-injectors increase the ease with which the user can carry out the injection, since many of the injection steps are automated.

The injection device of the present invention may use a needle to administer the injection. In such a case, it is preferred that the needle remains covered within the injection device prior to administration of the injection, and when the injection device is in its locked state. This reduces the possibility of accidental needle pricks. When the injection device is put into its unlocked state, by moving the release mechanism from its first position to its second position, it is then possible for the needle to be moved to an uncovered position as part of the injection process.

The housing can contain the fluid to be injected along with mechanisms of the injection device. The housing has a longitudinal axis that runs along the length of the housing. Further, the housing has a proximal end and a distal end.

The terms "proximal" and "distal" are used herein in relation to the person administering the injection. For example, when the injection is being administered by a user to a patient, the proximal end is the end closest to the user, while the distal end is the end furthest away from the user but closest to the patient who will receive the injection. Correspondingly, the housing is arranged such that the injection is delivered from its distal end. It should be noted that the use of the terms "proximal" and "distal" does not imply that the injection device cannot be used for self-administering an injection. In such a case, the distal end would still be defined as the end of the injection device that is closest to the target injection site immediately prior to the delivery of the injection.

The impediment may stop the action required to effect the injection from the injection device. For example, where the injection device is an auto-injector, the impediment may restrict the movement of the trigger which activates the injection cycle. Alternatively, the impediment may represent a barrier to the deliverance of the injection from the distal end of the housing of the injection device, i.e. the impediment may restrict the movement of an injection needle out of the housing and so prevent the injection cycle from being carried out.

The impediment may be in the form of a protrusion that impedes the delivery of the injection by blocking one of the motions required to administer the injection from the injection device. Such motions include the movement of a trigger for activating an auto-injector, the movement of the needle out of the injection device to penetrate the recipient's skin, the movement of the drive of an auto-injector, the movement of a syringe within the injection device, and the movement of a component, such as a syringe carrier, that moves the syringe within the injection device.

The release mechanism may be in the form of a switch, for example a rocker switch or a slide switch, where movement of the switch moves the impediment from its impeding position to its non-impeding position and, preferably, vice versa.

Alternatively, the release mechanism may comprise a movable sleeve, the sleeve being at least partially within the housing and protruding from the distal end of the housing. The moveable sleeve moving proximally along the longitudinal axis of the housing when moving the release mechanism from the first position to the second position. The sleeve may be in the form of a cylindrical element. Further, the cylindrical sleeve may have its longitudinal axis aligned parallel with the longitudinal axis of the housing, or additionally may have its longitudinal axis coincident with the longitudinal axis of the housing. Such a form for the moveable sleeve ensures the force required to move the sleeve is distributed over a large area, i.e. the circumference of the protruding end of the moveable sleeve, while not interrupting the deliverance of the injection through the hollow centre and along the longitudinal axis of the cylinder.

A release mechanism in the form of a movable sleeve protruding from the distal end of the housing can be moved by pushing the protruding sleeve against the skin of the intended recipient of the injection. This can cause the required movement of the movable sleeve to place the injection device in its unlocked state. This is a straightforward approach for moving the release mechanism from its first position to its second position as part of the injection procedure.

It is further preferred that the movable sleeve protrudes from the distal end when in the first position and is flush with the distal end of the housing when in the second position. This maximises the range of movement of the movable sleeve for a given protrusion distance and offers a further visual indication as to whether the release mechanism has been fully moved into the second position prior to attempting to deliver the injection.

A force needs to be applied to the release mechanism in order to move it from its first position to its second position. This force can vary as the release mechanism is moved from its first position to its second position. This variation in the force required to move the release mechanism can be represented by a force profile, which is the variation in force with distance moved by the release mechanism. The direction of movement of the release mechanism is usually into the injection device (i.e. proximally). In the present invention, this force profile may be non-linear. In other words, the force required to move the release mechanism is not proportional to the distance moved by a release mechanism. This is in contrast to prior art injection devices, which are based on linear-elastic behaviour.

The use of a non-linear variation produces tactile feedback that can allow the user to intuitively assess the progress of the release mechanism from its first position to its second position.

Therefore, the user can learn the feeling of the force profile associated with moving the release mechanism from its first position to its second position. The user can then use their knowledge of this feedback to assess whether the release mechanism has been successfully moved from its first position to its second position, and thus assess whether the injection device is ready for administering an injection. This reduces the likelihood that the user will attempt to perform an injection when the injection device is still in its locked state.

Alternatively or in addition, the injection device may produce audible feedback, in the form of an audible signal, when the release mechanism moves from the first position to the second position. The user will then be able to use this audible feedback to assess when the injection device is ready for administering an injection. In particular, an audible signal may sound when the release mechanism reaches the second position and the impediment is in a non-impeding position. The use of a non-linear variation in the force profile may produce the audible feedback that aids the user in assessing the progress of the release mechanism from its first position to its second position. This is further described below. Alternatively, or in addition, the audible signal may be effected by other means, for example the audible signal could be effected by certain components of the injection device contacting, leading to production of the audible signal. The contact of these components may complete an electrical circuit leading to the electronic production of an audible signal such as an electronic tone or beep. The contact of these components may initiate a mechanical mechanism that produces an audible signal, such as the impact of a hammer on a bell.

The non-linear force profile may be provided by the release mechanism having a resilient member that runs along a camming surface, wherein the combination of the resilient member and the camming surface is configured to produce the desired force profile. For example, the camming surface could be configured with one or more undulations, in the form of bumps or indents, which cause a specific variation in the force profile as the resilient member runs along this feature of the camming surface. The bumps and indents on the camming surface can also provide an audible signal, indicating the resilient member's progress along the camming surface. The camming surface may have one bump/indent, or two bumps/indents, or three bumps/indents or four or more bumps/indents. The camming surface may have a combination of bumps and indents. The camming surface may be curved, which can provide the non-linear force profile.

Alternatively or in addition, the non-linear force profile can be provided by the resilient member encountering a varying amount of frictional force as it progresses along the camming surface. For example, the resilient member may encounter an increasing amount of frictional force and/or a decreasing amount of frictional force, contributing an increasing force and/or decreasing force to the force profile as the release mechanism moves from the first position to the second position. The variation in frictional force can be achieved by varying the roughness of the camming surface portion along which the resilient member runs and/or varying the material of the camming surface portion along which the resilient member runs.

The variation in frictional force may cause the non-linear force profile on its own, or it can be used in combination with other methods of varying the force profile, such as the presence of undulations described above.

The injection device may have more than one set of resilient member and camming surface, i.e. there could be two resilient members with respective camming surfaces, or three or four resilient members with respective camming surfaces. When there is more than one set of resilient member and camming surface, each set may independently have any of the features described herein.

Further details of the possible forms of the force profile are given below. Other approaches for varying the force profile are within the scope of this invention.

The release mechanism may be resiliently biased towards the first position. In this way, the impediment that is coupled to the release mechanism is biased towards its impeding position. This ensures that a positive action has to occur in order to enable an injection to be administered from the injection device of the present invention, further reducing the possibility of accidentally delivering the injection.

The resilient bias towards the first position may be provided by a resilient member of the release mechanism experiencing increased deformation as it is moved from the first position to the second position. In other words, the deformation of the resilient member of the release mechanism may increase when the sleeve moves from the first position to the second position. The resilient bias is then driven by the relief of this deformation. It is preferable that this resilient member is the same used for providing the non-linear force profile detailed herein.

The force profile associated with the injection device of the present invention may exhibit an increasing force when the release mechanism is moved from the first position to the second position. Examples of two such force profiles are given in FIG. 1. Alternatively, or in addition, the force profile may exhibit a decreasing force when the release mechanism is moved from the first position to the second position. The force may continuously increase, or continuously decrease, as the release mechanism is moved from the first position to the second position. The force may continuously vary as the release mechanism is moved from the first position to the second position.

In particular, the force may continuously vary as the release mechanism is moved through its full range of movement, i.e. from being fully in its first position to being fully in its second position. An example of a force profile that exhibits both an increasing force and a decreasing force as the release mechanism moves from the first position to the second position is given in FIG. 2.

Utilising a force profile with a combination of increasing and decreasing forces, such as depicted in FIG. 2, can provide a particularly distinct tactile and audible feedback to the user since the force required to move the release mechanism varies periodically. The user will be able to readily discern the various increases and decreases in required force and so will, with experience, be able to use the tactile and audible clues to know when the release mechanism has been sufficiently moved so as to be in its second position.

In its simplest form, such a force profile would have a force that first increases and then decreases as the release mechanism is moved from the first position to the second position. Therefore, the skilled person would be able to feel completion of the required movement and so know that the injection device had been placed in the unlocked state.

Regarding the force profile depicted in FIG. 2, the user of an injection device with such a force profile can learn that after experiencing three of these periods, the injection device will be in its unlocked state and the injection can be delivered.

A similar effect can be achieved by using a force profile that is always increasing (or decreasing) but exhibits a variation in the rate of increase in the force with distance (i.e. a variation in the gradient of the force profile). Such a profile is depicted in FIG. 3, where there is a periodic variation in the rate of increase of the force with distance. First it increases and then it decreases before increasing and decreasing three more times. This variation can provide the tactile and audible feedback that informs the user of the progress of the release mechanism towards its second position and the unlocked state.

In its simplest form, such a force profile would have a force profile gradient that first increases and then decreases as the release mechanism is moved from its first position to its second position. After sensing the one increase and decrease, the user will know that the release mechanism has been moved a sufficient distance into its second position and the injection can be administered.

Regarding the force profile depicted in FIG. 3, the user can learn that after experiencing four of these periods, the injection device will be in its unlocked state and the injection can be delivered.

A force that changes from increasing with distance moved by the release mechanism to decreasing with distance moved by the release mechanism (or vice versa), and a force gradient that changes from increasing with distance moved by the release mechanism to decreasing with distance moved by the release mechanism (or vice versa) are both forms of periodic variation of the force profile that can be used with the present invention.

The force profile may have any number of periodic variations. As stated above, in its simplest form there will be just one increase and one decrease. Alternatively, there can be two increases and decreases, or three increases and decreases (as depicted in FIG. 2), or four or more increases and decreases (as depicted in FIG. 3).

The use of a plurality of periodic variations results in a ratchet-type effect as the force varies with distance giving a repetitive nature to the tactile and/or audible feedback. This assists the user in assessing the progress of the release mechanism from the first position to the second position.

All of the force profiles described herein allow the user to feel the progress of the release mechanism from the first position to the second position. Therefore the user is able to learn this feeling and subsequently ensure that the release mechanism is moved from the first position to the second position before administration of the injection is attempted.

The injection device may further comprise an activation means for effecting commencement of the injection, wherein the impediment interacts with a component of the activation means when it is in the impeding position so as to impede the activation means and so impede the delivery of the injection.

The activation means may comprise a trigger, the trigger being configured to be movable into an active position in order to effect the delivery of an injection from the injection device. The trigger could be in the form of a rocker switch or a slide switch or any equivalent form.

The activation means may comprise a drive which can provide the force required to deliver the injection. The drive may be in the form of a spring. The spring may be held in a state of compression prior to the delivery of the injection. During the delivery of the injection the spring is allowed to expand exerting the force which effects the delivery of the injection from the injection device.

As described above, in order to impede the delivery of the injection, the impediment of the injection device of the present invention may interact with a component of the activation means. For example, the impediment may interact with the trigger. Hence, the impediment when in the impeding position may stop the trigger from being moved into its active position. When the impediment is moved into its non-impeding position the trigger can then move to the active position and effect the commencement of the injection.

Alternatively, the impediment could interact with the drive which provides the force required to deliver the injection. For example, the impediment could stop the drive, in the form of a spring, from expanding and so stop the injection from being delivered.

As noted above, the release mechanism may comprise a resilient member and a camming surface upon which the resilient member is configured to ride along as the release mechanism is moved from the first position to the second position. In this way, the riding of the resilient member on the camming surface results in the force profile, and so the camming surface and the resilient member can be configured to provide any desired force profile. For example, the camming surface can be adjusted so that the resilient member experiences a varying amount of deformation as it rides along the camming surface and therefore results in a varying amount of force resisting its motion resulting in the force profile. Possible features on the camming surface are at least one bump and/or at least one indent.

The resilient member may not continuously ride along the camming surface as the release mechanism is moved from its first position to its second position. For example, the resilient member may not ride along the camming surface when the release mechanism is initially moved from being fully in its first position but will engage and ride along the camming surface as it moves fully into its second position, engaging the camming surface for the first time somewhere between the first position and the second position. This non-continuous riding of the resilient member on the camming surface will contribute to the non-linear nature of the force profile. Alternatively, the resilient member may be initially engaged with the camming surface but become disengaged as the release mechanism moves from its first position to its second position.

The resilient member may be in the form of a resilient arm, which acts as a cantilever with its free end running along the camming surface. Therefore, the various features on the camming surface result in varying degrees of bending of the cantilever and so varying degrees of deformation resulting in a particular force profile. The resilient member/arm is part of the release mechanism and so will move when the release mechanism moves. The resilient member/arm may be integrally formed with the release mechanism. This simplifies the manufacturing process of the injection device.

The camming surface and resilient arm may be configured such that the resilient arm is deformed within a two-dimensional plane. In particular, the resilient arm may be configured to run along the camming surface in the proximal direction and distal direction of the injection device when the release mechanism is moved in the proximal direction and distal direction of the injection device respectively. An example of such an arrangement has the camming surface on the inside of the housing and generally inclined towards the longitudinal axis of the housing, the inclination increasing along the longitudinal direction of the housing. As the resilient arm runs along the camming surface, the general incline causes the resilient member to be deformed towards the central longitudinal axis, in the radial direction.

Alternatively, the camming surface can be arranged on the internal surface of the housing in a generally circumferentially inclined manner, preferably around the longitudinal axis of the housing.

The resilient arms then run along the generally circumferentially inclined camming surface in a generally circumferential direction when the release mechanism is moved in the proximal and distal directions of the injection device. If the rotational movement of the release mechanism is constrained, the deformation of the resilient arms in the generally circumferential direction is maximised. This generally circumferential arrangement reduces the diametrical space requirement of the camming surface/resilient arm mechanism, since the resilient arms do not need to bend towards the centre of the housing but instead run around the internal surface of the housing.

The form of camming surfaces described above may have undulations or exhibit a varying amount of friction influencing the force profile observed when moving the resilient arms along the camming surface.

Even if the camming surfaces described above have undulations or exhibit varying amounts of friction along the camming surface, the general incline of the surface means that the resilient member is more deformed when the release mechanism is in its second position compared to when it is in its first position. In other words, as the release mechanism moves from its first position to its second position, there is a general trend of increased deformation in the resilient member.

The injection device may be configured to receive a syringe. In particular, the injection device may be configured to receive a hypodermic syringe. To this end, the injection device may further comprise a syringe carrier, which can hold a syringe within the injection device and carry the syringe during the delivery of the injection.

Where the injection device is configured to receive a syringe, the impediment may act on the syringe in order to impede the delivery of the injection when the impediment is in its impeding position. When the injection device comprises a syringe carrier, the impediment may act on the syringe carrier in order to impede the injection when the impediment is in its impeding position.

A third aspect of this invention provides an injection kit comprising an injection device of the present invention and a syringe. In particular, the syringe may be a hypodermic syringe. The injection device in the injection kit is configured to receive the syringe that is present in the injection kit. The injection device that forms part of the injection kit may have any of the features described above.

A fourth aspect of the present invention provides a method of operating an injection device of the present invention, comprising the steps of moving the release mechanism from the first position towards the second position; and delivering the injection after detecting the audible signal. The injection device utilised with this method may have any of the features described above.

A fifth aspect of the present invention provides a method of operating an injection device of the present invention, comprising the steps of moving the release mechanism from the first position towards the second position and delivering the injection after detecting the non-linear nature of the force profile. The injection device utilised with this method may have any of the features described above.

The methods of the present invention allows the user to learn from experience the tactile and/or audible feedback caused by the non-linear nature of the force profile, which indicates that the release mechanism has moved fully from its first position to its second position indicating that the injection can be successfully delivered. Therefore, the user is able to ensure that the release mechanism has been fully moved into its second position avoiding the problems associated with prior art devices.

The injection device or injection kit of any of the above embodiments may contain a substance selected from the group consisting of: golimumab, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

By 'the injection device or injection kit may contain a substance' it is meant that the substance may be contained within a suitable medicament container, such as a vial or syringe, within the injection device, or within the syringe of the injection kit. Such medicament container may contain other substances, such as further active or inactive ingredients.

In a further aspect of the invention, a substance is provided, the substance being selected from the group consisting of: golimumab, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity, by delivery of said substance to a human subject using an injection device or injection kit according to any of the above embodiments.

In yet another aspect of the invention, an injection device is provided for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity, by delivery of a substance selected from the group consisting of: golimumab, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, to a human subject by using the injection device, where the injection device is an injection device or injection kit of any of the above embodiments.

By 'delivery of a substance' it is meant that the injection device is used to inject said substance into the human subject, for example by subcutaneous, intradermal or intramuscular injection. Said substance may be administered in combination with other substances, such as further active or inactive ingredients.

BRIEF DESCRIPTION OF THE DRAWINGS

The present invention is now described by way of example with reference to the accompanying drawings, in which:

FIG. 8 depicts the detail of a bump on the camming surfaces of an injection device of the present invention;

FIG. 9 depicts the force profile resulting from the combination of resilient arms and camming surfaces depicted in FIG. 8;

FIG. 16 depicts a possible arrangement of the camming surfaces and resilient arms where the frictional forces exerted by the camming surface change along its length;

FIG. 17 depicts the resulting force profile from the arrangement of FIG. 16;

FIG. 20 depicts the detail of a spring arrangement of an injection device of the present invention; and FIG. 21 depicts the force profile resulting from the spring arrangement of FIG. 16.

DETAILED DESCRIPTION OF THE DRAWINGS

Figure 1:
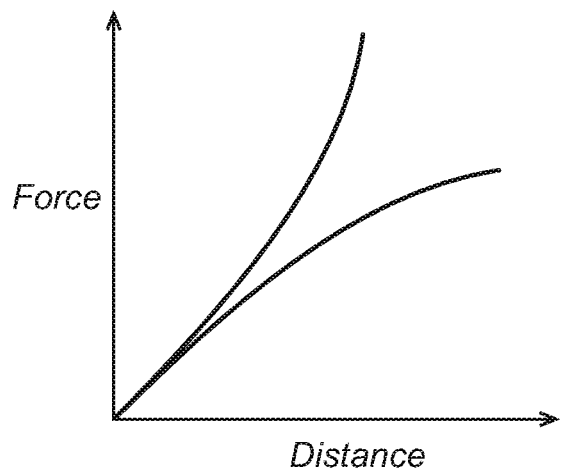
FIG. 1 depicts an example of two forms of force profiles, one with an increasing gradient and one with a decreasing gradient.
Figure 2:
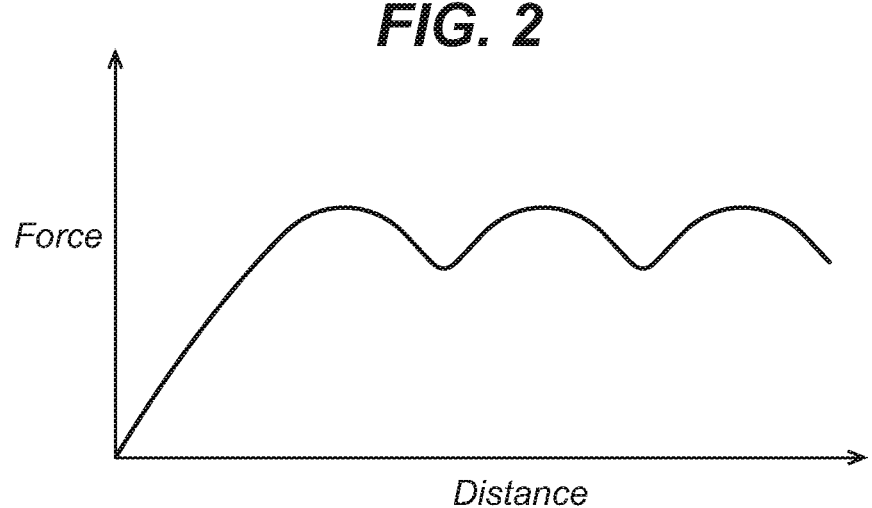
FIG. 2 depicts a force profile that exhibits an increasing force followed by a decreasing force, then the force increases and decreases two more times.
Figure 3:
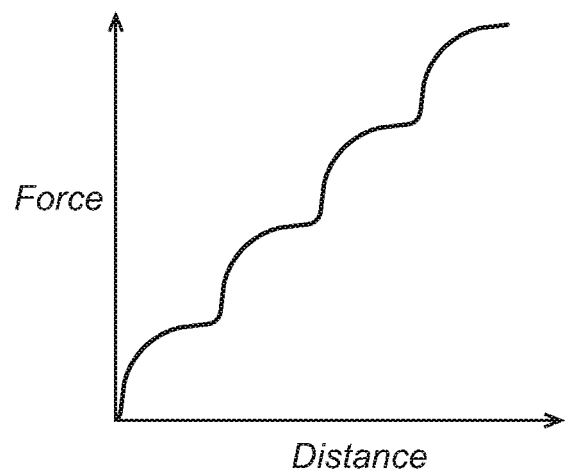
FIG. 3 depicts a force profile where the rate of increase in the force first increases then decreases, then increases and decreases three more times.
Figure 4:
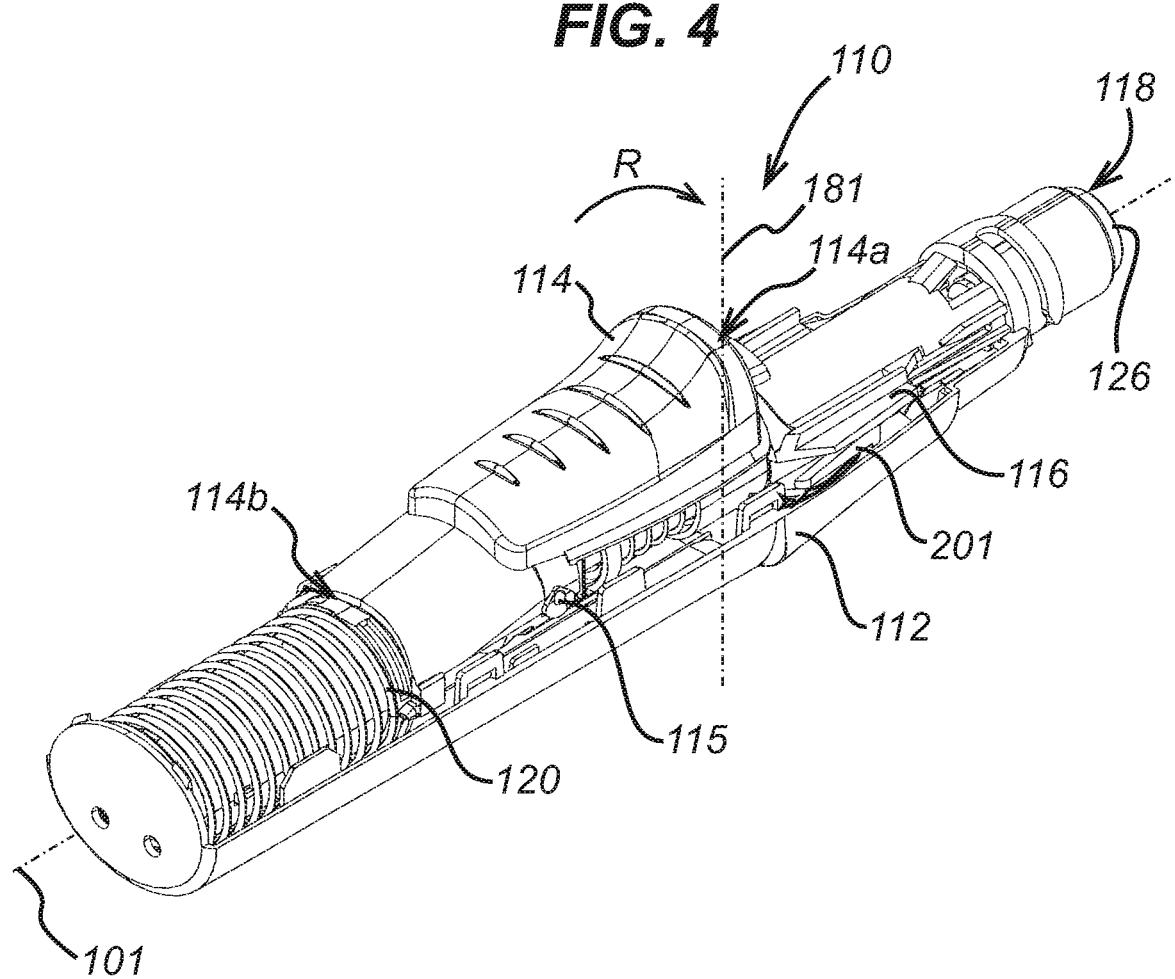
FIG. 4 depicts an injection device of the present invention showing the mechanism within the housing.
Figure 5:
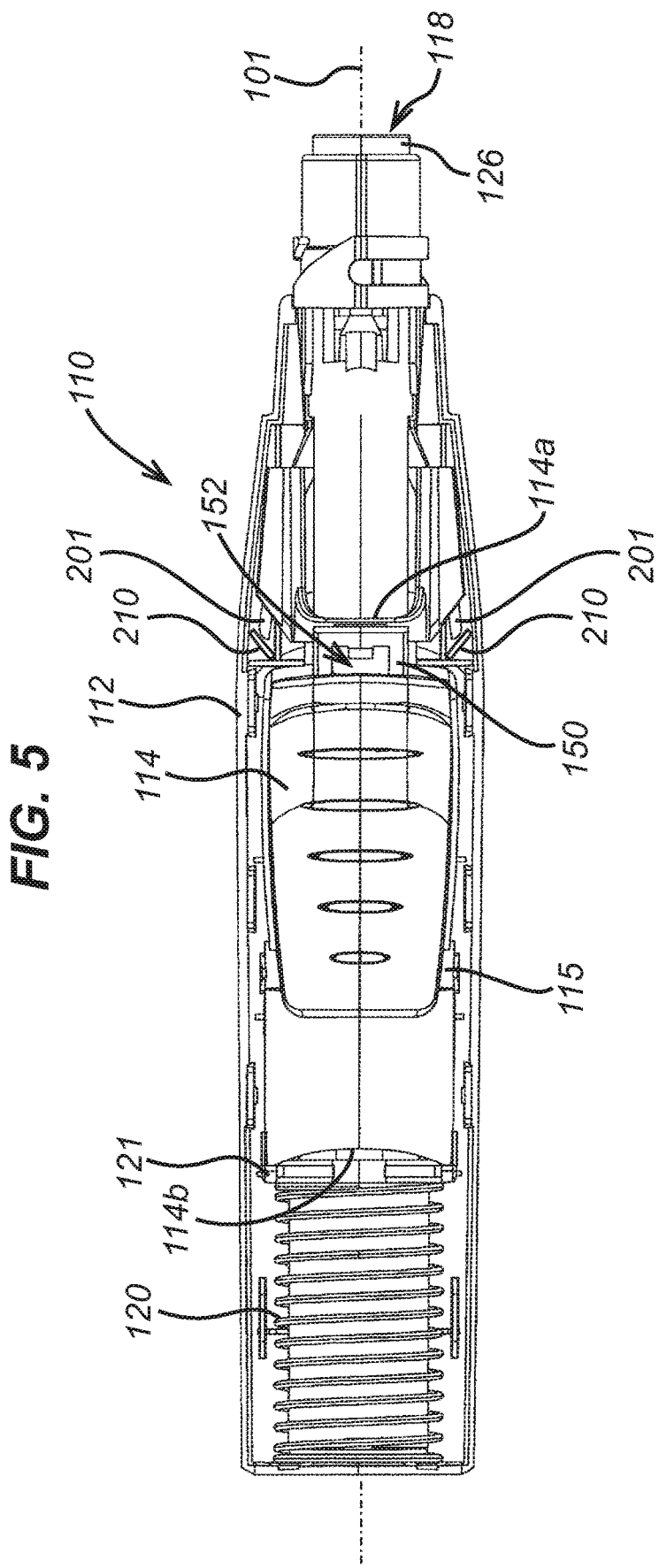
FIG. 5 depicts a plan view of an injection device of the present invention.

An injection device 110 according to the present invention is depicted in FIGS. 4 and 5. The injection device 110 has an injection device housing 112 and a longitudinal axis 101.

FIGS. 4 and 5 depict only the lower half of the housing 112. The upper part of housing 112 is absent so that the internal mechanism can be clearly seen.

A syringe (not shown) is contained in the housing 112. The injection device 110 comprises a trigger 114 as part of the activation means. The trigger 114 is rotatable about a pivot 115 from a rest position (as shown in FIG. 4) to an active position. The proximal end 114b of the trigger 114 connects with a drive coupling 121 which is acted upon by a drive spring 120. The drive coupling 121 is in communication with the syringe. The drive coupling 121 and drive spring 120 all form part of the activation means which allow the delivery of the injection by acting on the syringe.

The injection device 110 comprises a release mechanism 126 in the form of a cylindrical sleeve that protrudes from the distal end of the injection device 110.

In order to effect delivery of the injection, the trigger 114 is rotated about the pivot 115 in a direction R (i.e. downwards into the housing 112 at its first end 114a). This causes the second end 114b of the trigger 114 to disengage from the drive coupling 121, thereby letting the drive spring 120 drive the syringe (via the drive coupling 121) along the longitudinal axis 101 and out of an aperture 118 in the housing 112.

Figure 6:
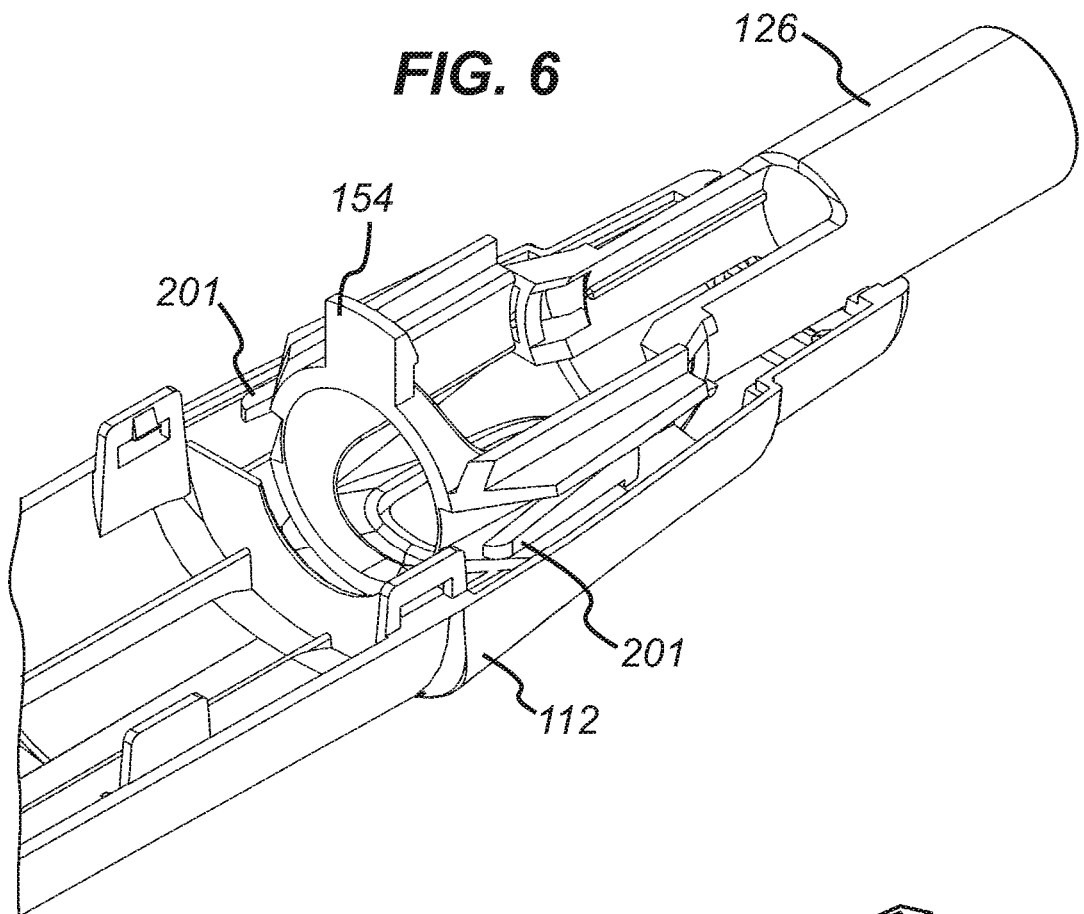
FIG. 6 depicts the detail of the release mechanism of an injection device of the present invention.

However, when the release mechanism 126 is in its impeding position, which corresponds to the release mechanism protruding from the distal end of housing 112, an impediment in the form of a protrusion 154 (as depicted in FIG. 6) is positioned so as to abut the under-surface of portion 150 of trigger 114. In this way, the protrusion 154 impedes the rotation of the trigger and thus impedes the delivery of the injection. In order to carry out the injection, the release mechanism is moved into a second position, which corresponds to the release mechanism 126 being moved into the housing 112 along the direction of the longitudinal axis 101. When the release mechanism is in its second position the protrusion 154 aligns with cut out 152 in trigger 114. Protrusion 154 can be received in cut out 152 and so the trigger can be rotated about pivot 115 and the delivery of the injection can be effected.

Figure 7:
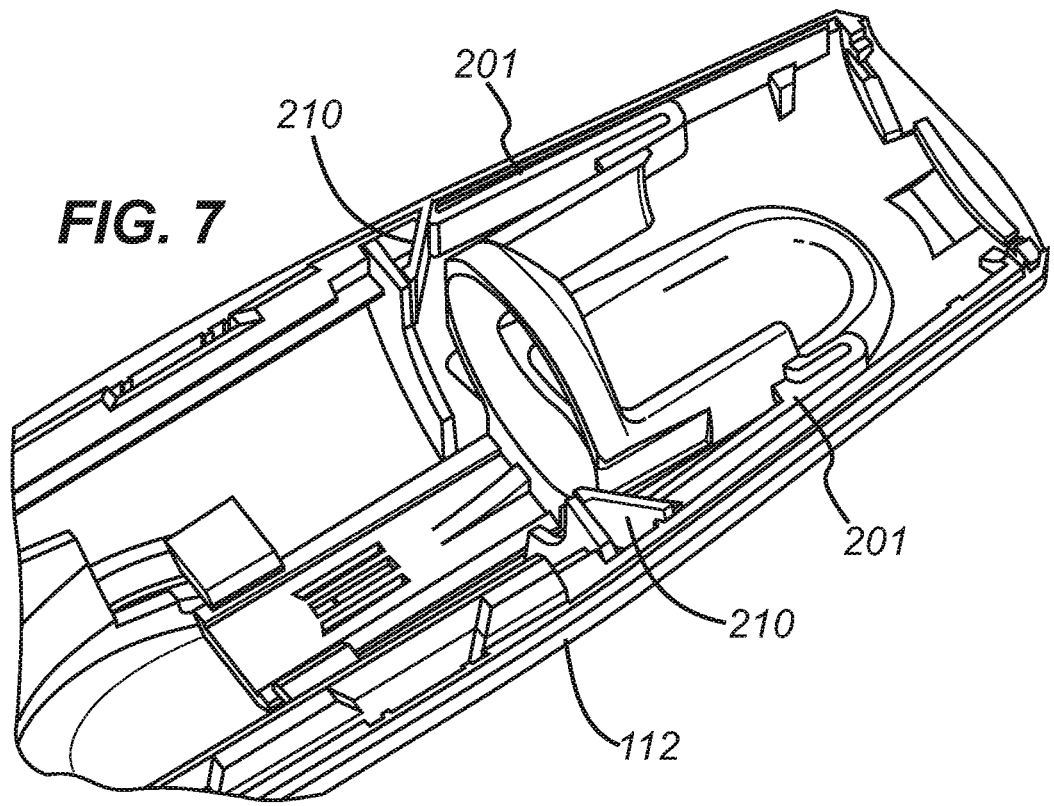
FIG. 7 depicts a detailed view of parts of the release mechanism of an injection device of the present invention.

As can be seen in FIGS. 6 and 7, the release mechanism 126 is provided with a pair of intregrally formed resilient arms 201 in the form of cantilevers. The resilient arms 201 are configured to resiliently flex in a direction towards and away from the housing 112.

The housing 112 comprises a pair of camming surfaces 210 along which the resilient arms 201 will ride when the release mechanism 126 is moved from its first position in which the protrusion 154 abuts the portion 150 of the trigger 114 to its second position where the protrusion 154 can be received in the cut out portion 152 of the trigger 114. As can be seen from FIG. 7, the deformation in resilient arms 201 increases as the release mechanism 126 is moved from its first position to its second position, i.e. as the release mechanism 126 is moved into the housing 112 along the longitudinal axis 101 of the injection device 110. This provides a resilient bias on the release mechanism 126 towards its first position.

Detail of a possible form of the camming surface is shown in FIG. 8. Here it can be seen that the camming surfaces 210 comprise bumps 212. These bumps 212 introduce a non-linear variation in the force with distance moved by the release mechanism 126. In particular, the bumps 212 will result in a force profile that has a rate of increase in force that first increases and then decreases as depicted in FIG. 9. This non-linear force profile results in a tactile feedback to the user which indicates that the release mechanism 126 has been fully moved from its first position to its second position and activation of the injection cycle can occur.

Figure 11:
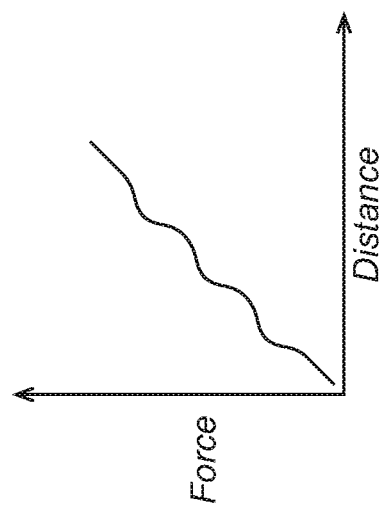
FIG. 11 depicts the force profile resulting from the combination of resilient arms and camming surfaces depicted in FIG. 10.
Figure 10:
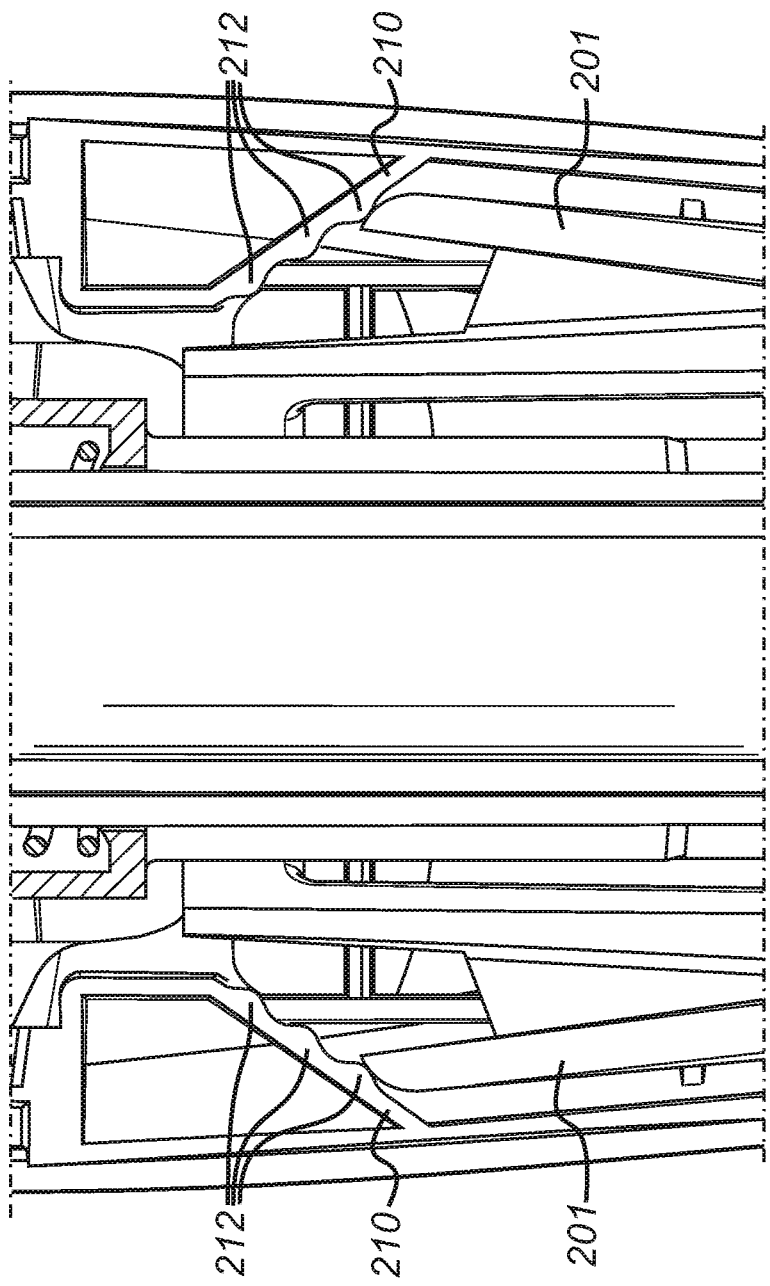
FIG. 10 depicts the detail of a plurality of bumps on the camming surface of an injection device of the present invention.

An alternative form of the camming surface is shown in FIG. 10. Here it can be seen that each camming surface 210 comprises three bumps 212. These three bumps 212 result in a force profile with a periodic, ratchet-type nature where the rate of increase in force first increases and then decreases, and then increases and decreases two more times, as depicted in FIG. 11.

Figure 13:
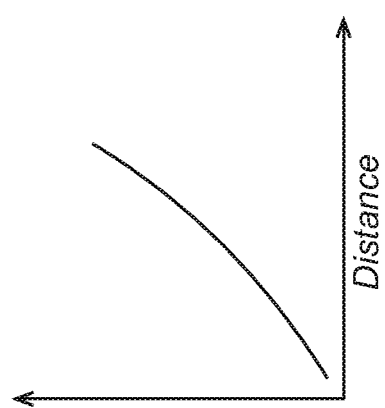
FIG. 13 depicts the force profile resulting from the combination of resilient arms and camming surfaces depicted in FIG. 12.
Figure 12:
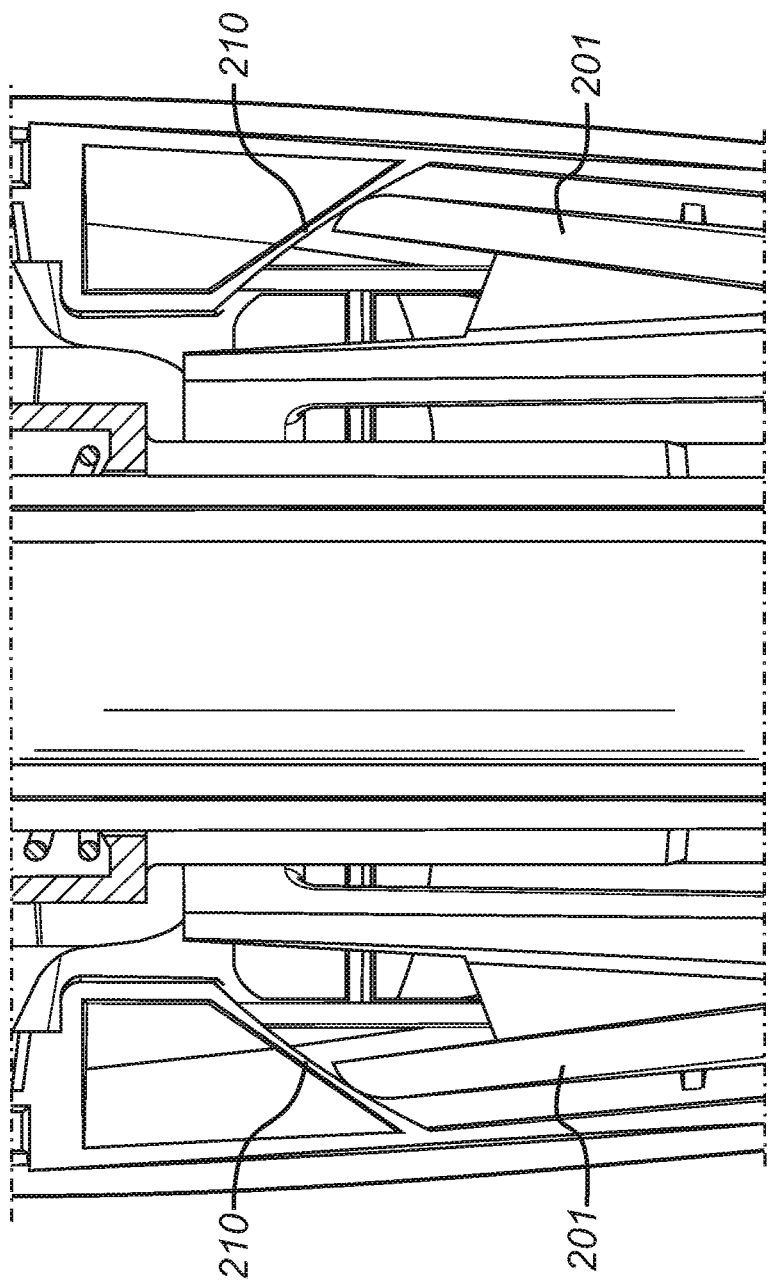
FIG. 12 depicts the detail of curved camming surfaces of an injection device of the present invention.

A further possible form of the camming surface is shown in FIG. 12. In this example, the camming surface doesn't have any bumps but instead has a continuous curved surface which increases the rate of deformation of the resilient arms 201 as the release mechanism 126 is moved from its first position to its second position. This results in the force profile depicted in FIG. 13, where the force continuously increases with distance and the rate of increase in the force also continuously increases with distance. As with the other force profiles, this provides tactile feedback that helps the user assess the progress of the release mechanism 126 from its first position to its second position.

Figure 14:
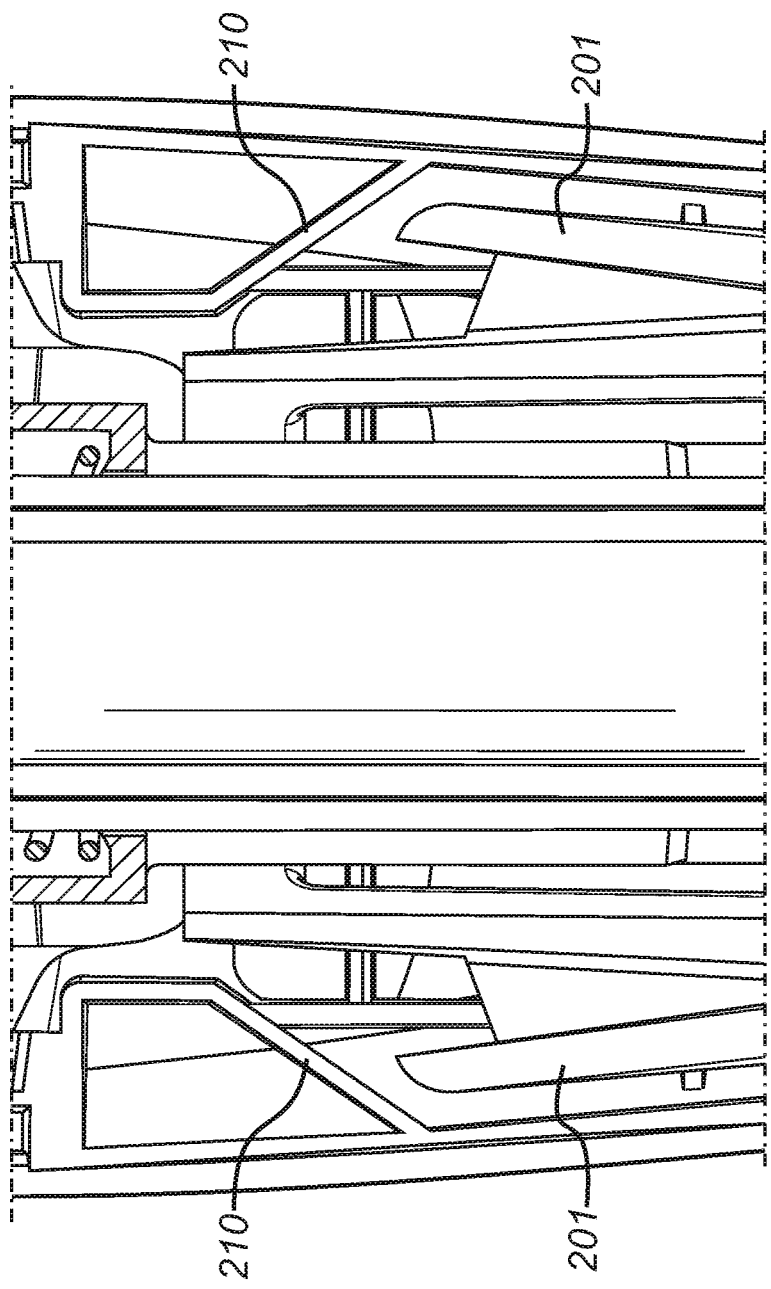
FIG. 14 depicts another possible arrangement of camming surfaces and resilient arms.
Figure 15:
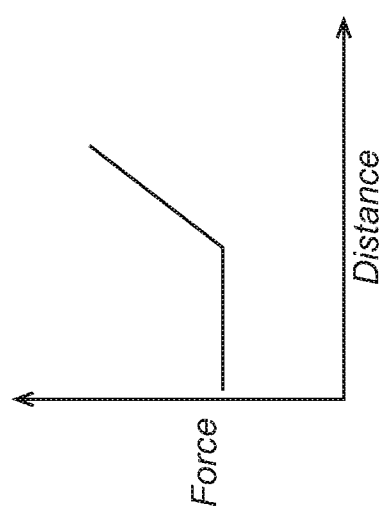
FIG. 15 depicts the resulting force profile from the arrangement of FIG. 14.

Yet another possible arrangement of camming surfaces and resilient arms is depicted in FIG. 14. In this example, the resilient arms 201 do not contact the camming surfaces 210 when the release mechanism 126 is fully in its first position (as shown in FIG. 14). Therefore, the initial part of the force profile is a relatively constant force, which is caused by the frictional forces associated with moving the release mechanism 126. The force profile then demonstrates an increasing force as the release mechanism 126 is moved further towards its second position and the resilient arms 201 engage and ride along the camming surfaces 210. The resulting force profile is depicted in FIG. 15.

A further possible arrangement of camming surfaces and resilient arms is depicted in FIG. 16. Here the resilient arms (201) are always in contact with the camming surfaces (210) but there is a step-change in the frictional force between the resilient arms (201) and the camming surfaces (210) along the path which the resilient arms run. This results in a step-change in the resulting force profile, as depicted in FIG. 17.

Figure 18A:
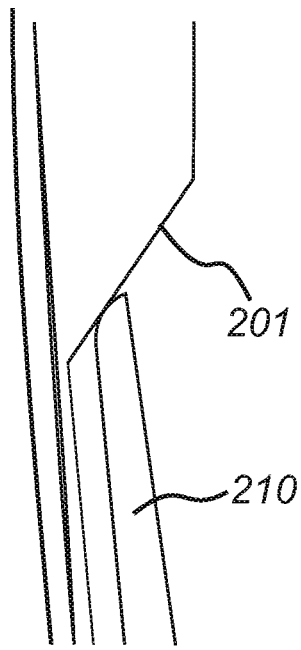
FIGS. 18a, b and c depict the movement of the resilient arm relative to a camming surface inclined towards the longitudinal axis of the injection device.
Figure 18B:
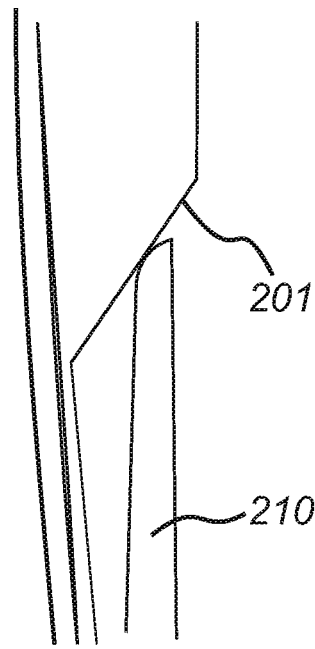
Figure 18C:
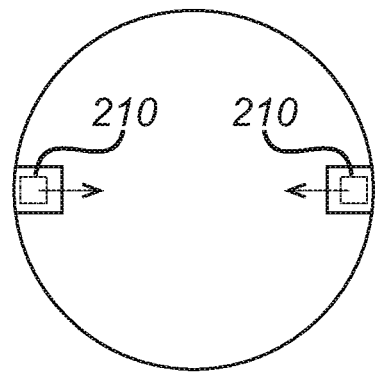

The injection device can have a camming surface 201 inclined towards the longitudinal axis of the housing of the injection device, as depicted in FIG. 18a. The inclination increasing along the longitudinal direction of the housing. This results in the resilient arm 210 being bent towards the longitudinal axis of the housing in a two-dimensional plane when the arm is moved along the camming surface 201 in a proximal direction, as illustrated in FIG. 18b. A cross-sectional view of the housing, perpendicular to the longitudinal axis of the housing, shows the radial direction in which the resilient arms 210 move.

Figure 19A:
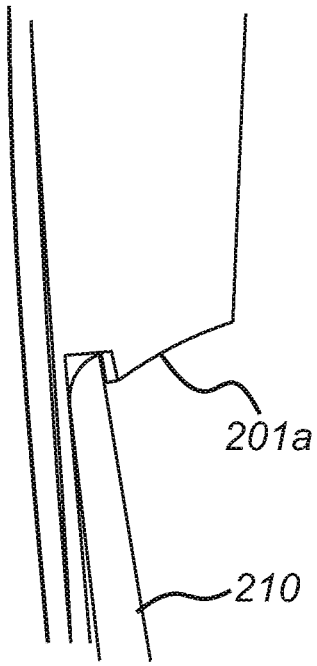
FIGS. 19a, b and c depict the movement of the resilient arm relative to a camming surface arranged in a circumferentially inclined manner.
Figure 19B:
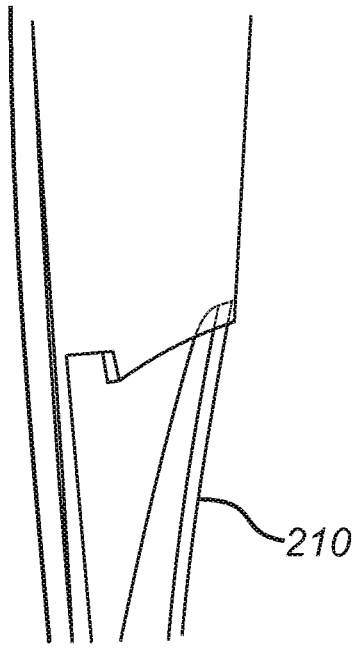
Figure 19C:
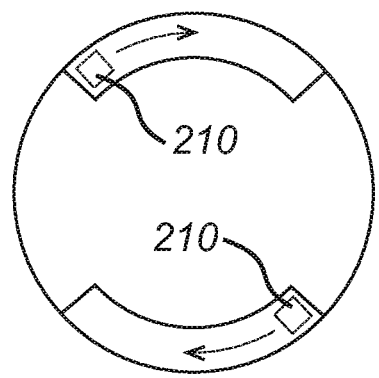

An alternative form of the camming surface is depicted in FIG. 19a. This camming surface 201a is arranged in a circumferentially inclined manner around the longitudinal axis of the housing, extending inwards from the inner surface of the housing. Hence the camming surface 201a is inclined such that the resilient arm 210 will run along the circumferential camming surface 201a as the resilient arm is moved into the housing. This results in the resilient arm 210 being deformed in a circumferential direction on moving along the camming surface, as depicted in FIG. 19b. A cross-sectional view of the housing (FIG. 19c), perpendicular to the longitudinal axis of the housing, shows the circumferential direction in which the resilient arms 210 move.

As described above, various force profiles can be realised by different configurations of resilient arms 201 and the camming surfaces 210. Further, force profiles can be realised by other means, such as arrangement of springs.

An example of such an arrangement of springs is given in FIG. 20. The release mechanism 126 has a first pair of springs 214 and a second pair of springs 216. When the release mechanism 126 is in its first position, only the first pair of springs 214 is constrained at both ends and so capable of exerting a force against the movement of the release mechanism 126 from its first position to its second position. However, as the release mechanism 126 is moved from its first position to its second position, the second pair of springs 216 is engaged resulting in a sudden increase in the rate of increase in the force as the release mechanism 126 continues to progress towards its second position. This results in the non-linear force profile depicted in FIG. 21.

In use, such an injection device as described above might be used to deliver substances such as: golimumab, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity. In addition to these substances, any medicament contained within the injection device may also include other substances, such as inactive ingredients, as a skilled person would appreciate.

It will of course be understood by the person skilled in the art that particular substances are efficacious for use in the treatment or prevention of particular conditions, as is well known in the art. For instance, it is known that antiallergics are efficacious for use in the treatment or prevention of allergies; antihistamines are efficacious for use in the treatment or prevention of hay fever; anti-inflammatories are efficacious for use in the treatment or prevention of inflammation; and so on. Accordingly, any selection of one or more substances listed herein or in the claims for use in the treatment or prevention of one or more conditions for which those substance(s) are known to be efficacious is envisaged.

In a particular example, however, golimumab is known to be efficacious for use in the treatment or prevention of one or more of rheumatoid arthritis, psoriatic arthritis, ankylosing spondylitis or ulcerative colitis, or any combination of rheumatoid arthritis, psoriatic arthritis, ankylosing spondylitis and ulcerative colitis, or all of rheumatoid arthritis, psoriatic arthritis, ankylosing spondylitis and ulcerative colitis.

Golimumab may optionally be used in combination with one or more inactive ingredients such as any or all of L-histidine, L-histidine monohydrochloride monohydrate, sorbitol, polysorbate 80, and water. Golimumab may present in a composition in which golimumab is the only active ingredient. For example, golimumab may administered as SIMPONI®.

It will of course be understood that the present invention has been described above purely by way of example and modifications of detail can be made within the scope of the invention.

The invention claimed is:

1. An injection device for delivering an injection comprising:
   a housing having a longitudinal axis, a proximal end and a distal end, the housing being arranged such that the injection is delivered from its distal end;
   an activation mechanism adapted to commence the injection, the activation mechanism comprising a trigger configured to be moveable into an active position so as to effect the delivery of the injection; and
   a release mechanism comprising an impediment that interacts with the trigger, the release mechanism being moveable between a first position, in which the impediment is in an impeding position so as to impede movement of the trigger to the active position, and a second position, in which the impediment is in a non-impeding position so as to not impede movement of the trigger to the active position, wherein the force required to move the release mechanism from the first position to the second position varies with the distance moved by the release mechanism, the variation in the force required with distance being represented by a force profile, which is non-linear.

2. An injection device according to claim 1, wherein the release mechanism is resiliently biased towards the first position.

3. An injection device according to claim 1, wherein the force profile exhibits an increasing force when the release mechanism is moved from the first position to the second position.

4. An injection device according to claim 1, wherein the activation mechanism comprises a drive to provide the force required to deliver the injection.

5. An injection device according to claim 1, wherein the injection device is configured to receive a syringe.

6. An injection device according to claim 2, wherein the release mechanism comprises a moveable sleeve, the sleeve protruding from the distal end of the housing and moving proximally along the longitudinal axis of the housing when moving the release mechanism from the first position to the second position.

7. An injection device according to claim 3, wherein the rate of increase in the force first increases and then decreases when the release mechanism is moved from the first position to the second position.

8. An injection kit comprising an injection device according to claim 5; and a syringe.

9. An injection device according to claim 6, wherein the moveable sleeve protrudes from the distal end when in the first position and is flush with the housing when in the second position.

10. An injection device according to claim 6, wherein the moveable sleeve comprises a resilient arm and the housing further comprises a camming surface inside the housing, the resilient arm being configured to ride along the camming surface as the moveable sleeve moves from the first position to the second position, the camming surface being configured such that the deformation of the resilient arm increases when the sleeve moves from the first position to the second position providing the resilient bias towards the first position.

11. An injection device according to claim 10, wherein the camming surface is generally inclined towards the longitudinal axis of the housing.

12. An injection device according to claim 10, wherein the camming surface is generally circumferentially inclined along the inner surface of the housing.

13. An injection device according to claim 10, wherein the camming surface has an undulation to provide the non-linear force profile.

14. An injection device for delivering an injection comprising:
a housing having a longitudinal axis, a proximal end and a distal end, the housing being arranged such that the injection is delivered from its distal end;
an activation mechanism adapted to commence the injection, the activation mechanism comprising a trigger configured to be moveable into an active position so as to effect the delivery of the injection; and
a release mechanism comprising an impediment that interacts with the trigger, the release mechanism being moveable between a first position, in which the impediment is in an impeding position so as to impede movement of the trigger to the active position, and a second position, in which the impediment is in a non-impeding position so as to not impede movement of the trigger to the active position, wherein the injection device produces an audible signal when the release mechanism is moved from the first position to the second position, wherein the force required to move the release mechanism from the first position to the second position varies with the distance moved by the release mechanism, the variation in the force required with distance being represented by a force profile, which is non-linear.

15. A method of operating an injection device of any of claims 1, 14, 7, or 4-5 comprising the steps of moving the release mechanism from the first position towards the second position; and
delivering the injection after detecting the non-linear nature of the force profile.

16. An injection device according to any one of claims 1, 14, 7, or 4-5 or an injection kit according to claim 8 containing a substance selected from the group consisting of: golimumab, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

17. An injection device for use in the treatment or prevention rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity, by delivery of a substance selected from the group consisting of: golimumab, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, to a human subject by using the injection device, wherein the injection device is an injection device according to any one of claims 1, 14, 7, or 4-5 or an injection kit according to claim 8.

* * * * *